(12) United States Patent
Isner

(10) Patent No.: US 7,125,856 B1
(45) Date of Patent: Oct. 24, 2006

(54) ANGIOGENIC GROWTH FACTORS FOR TREATMENT OF PERIPHERAL NEUROPATHY

(75) Inventor: Jeffrey M. Isner, Weston, MA (US)

(73) Assignee: St. Elizabeth's Medical Center of Boston, Inc., Boston, MA (US)

( * ) Notice: Subject to any disclaimer, the term of this patent is extended or adjusted under 35 U.S.C. 154(b) by 0 days.

(21) Appl. No.: 09/546,733

(22) Filed: Apr. 11, 2000

Related U.S. Application Data

(60) Provisional application No. 60/129,768, filed on Apr. 15, 1999.

(51) Int. Cl.
*A01N 43/04* (2006.01)
*A61K 31/70* (2006.01)

(52) U.S. Cl. ..................................................... 514/44

(58) Field of Classification Search .................. 514/44; 424/93.1, 93.2, 93.21
See application file for complete search history.

(56) References Cited

U.S. PATENT DOCUMENTS

| | | | |
|---|---|---|---|
| 5,219,739 A | 6/1993 | Tischer et al. | 435/69.4 |
| 5,420,112 A | 5/1995 | Lewis et al. | 514/12 |
| 5,604,202 A | 2/1997 | Kessler et al. | 514/12 |
| 5,607,918 A | 3/1997 | Eriksson et al. | 514/12 |
| 5,935,820 A | 8/1999 | Hu et al. | 435/69.4 |
| 6,013,780 A | 1/2000 | Neufeld et al. | 536/23.1 |

FOREIGN PATENT DOCUMENTS

| | | |
|---|---|---|
| WO | WO 92 11360 A1 | 7/1992 |
| WO | WO 97/19693 | 6/1997 |
| WO | WO 99/36103 | 7/1999 |

OTHER PUBLICATIONS

Apfel, SC (2001) Neurotrophic factor therapy: Prospects and problems. Clinical Chemistry and Laboratory Medicine 39(4): 351-355.*

Baumgartner et al. (1998) Constitutive expression of phVEGF-165 after intramuscular gene transfer promotes collateral vessel development in patients with critical limb ischemia. Circulation 97: 1114-1123.*

Friedmann, T. (Jun. 1997) Overcoming the obstacles to gene therapy. Scientific American, Jun. 1997, pp. 96-101.*

Isner et al. (1996) Clinical evidence of angiogenesis after arterial gene transfer of phVEGF-165 in patient with ischaemic limb. Lancet 348: 370-374.*

Orkin and Motulsky (1995) Report and recommendations of the panel to assess the NIH investment in research on gene therapy. pp. 1-40.*

Verma et al. (1997) Gene therapy—promises, problems, and prospects. Nature 389: 239-242.*

NINDS Peripheral Neuropathy Information Page (2001), pp. 1-3.*

Samii, Amir et al., "Vascular Endothelial Growth Factor Expression in Peripheral Nerves and Dorsal Root Ganglia in Diabetic Neuropathy in Rats," *Neuroscience Letter*, 262: 159-162 (1999).

Créange, Alain et al., "Cytokines and Peripheral Nerve Disorder," *Eur. Cytokine Netw.*, 8, 2: 145-151 (Jun. 1997).

Schratzberger, Peter et al., "Favorable Impact of Therapeutic Angiogenesis on Peripheral Ischemic Neuropathy,", Abstract. (Feb. 11, 1999).

Duh, Elia, "Vascular Endothelial Growth Factors and Diabetes: The Agonist Versus Antagonist Paradox," *Diabetes*, 48: 1899-1906 (Oct. 1999).

Lair JM et al, "Acidic fibroblast growth factor stimulates motor and sensory axon regeneration after sciatic nerve crush in the rat," *Neuroscience*, vol. 65, No. 1, 1995, pp. 209-216.

Schratzberger P et al., Favorable effect of VEGF gene transfer on ischemic peripheral neuropathy. *Nat Med* 6(4):405-413 (Apr. 2000).

Schratzberger P et al., Reversal of experimental diabetic neuropathy by VEGF gene transfer. *J Clin Invest* 107(9):1083-1092 (May 2001).

Sondell M et al., Vascular endothelial growth factor has neurotrophic activity and stimulates axonal outgrowth, enhancing cell survival and Schwann cell proliferation in the peripheral nervous system. *J Neurosci* 19(14):5731-5740 (Jul. 15, 1999).

Yang, Xiu-Ming et al., "Autocrine Hepatocyte Growth Factor Provides a Local Mechanism for Promoting Axonal Growth," *The Journal of Neuroscience*, Oct. 15, 1998, 18(20), pp. 8369-8381.

* cited by examiner

*Primary Examiner*—Anne-Marie Falk
(74) *Attorney, Agent, or Firm*—Wolf, Greenfield & Sacks, P.C.

(57) ABSTRACT

A method for treating peripheral neuropathy, particularly ischemic peripheral neuropathy, is provided. The method involves administering to subjects in need of such treatment an effective amount of an angiogenic growth factor to alleviate a symptom of the neuropathy.

4 Claims, 1 Drawing Sheet

SEQUENCE LISTING

<160> NUMBER OF SEQ ID NOS: 2

<210> SEQ ID NO 1
<211> LENGTH: 22
<212> TYPE: DNA
<213> ORGANISM: homo sapiens

<400> SEQUENCE: 1
gagggcagaa tcatcacgaa gt                    22

<210> SEQ ID NO 2
<211> LENGTH: 22
<212> TYPE: DNA
<213> ORGANISM: homo sapiens

<400> SEQUENCE: 2
tcctatgtgc tggccttggt ga                    22

ANGIOGENIC GROWTH FACTORS FOR TREATMENT OF PERIPHERAL NEUROPATHY

RELATED APPLICATIONS

Figure 1A:
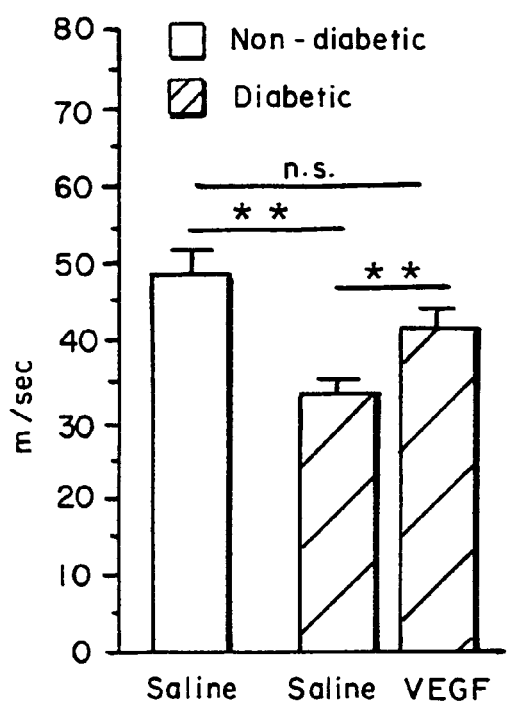

This application claims priority under Title 35 §119(e) of United States Provisional Application No. 60/129,768, filed Apr. 15, 1999, and entitled ANGIOGENIC GROWTH FACTORS FOR TREATMENT OF PERIPHERAL NEUROPATHY, the entire contents of which are incorporated herein by reference.

GOVERNMENT SUPORT

Some aspects of the present invention were made with support by a grant from the United States National Institutes of Health (NIH) under NIH grant HL053354. The U.S. Government retains certain rights in the invention.

FIELD OF THE INVENTION

This invention relates to methods and compositions for the treatment of peripheral neuropathy, such as ischemic peripheral neuropathy. The methods involve administering an angiogenic growth factor to alleviate a symptom of a peripheral neuropathy and, optionally, enhance nerve regeneration in a mammal.

BACKGROUND OF THE INVENTION

Peripheral neuropathy generally refers to a disorder that affects the peripheral nerves, most often manifested as one or a combination of motor, sensory, sensorimotor, or autonomic neural dysfunction. Peripheral neuropathies can be genetically acquired, can be induced by a toxic agent, or can result from peripheral ischemia or from a systemic disease. Genetically-acquired peripheral neuropathies include Refsum's disease, Abetalipoproteinemia, Tangier disease, Krabbe's disease, Metachromatic leukodystrophy, Fabry's disease, Dejerine-Sottas syndrome, Charcot-Marie Tooth Disease (also known as Peroneal Muscular Atrophy, or Hereditary Motor Sensory Neuropathy) and others. Exemplary toxic agents which cause neurotoxicities include therapeutic drugs such as antineoplastic agents, contaminants in foods, and environmental and industrial pollutants. Ischemic peripheral neuropathies include, but are not limited to, diabetic polyneuropathy. Peripheral neuropathies associated with a systemic condition include uremia and alcoholic polyneuropathy among other disorders.

Ischemic peripheral neuropathy, particularly when it develops in the absence of diabetes, has received limited study, despite the fact that it may be a prominent feature of patients with peripheral vascular disease. Among diabetics, peripheral neuropathy is common and ultimately accounts for significant morbidity. Typically, symptoms are dominated by sensory defects. (Tomlinson DR, et al. *Diabetes* 1997;46:S43–S49). The ultimate consequence of such sensory deficits involving the lower extremities may be foot ulceration initiated by traumatic injury that is inapparent to the patient. Indeed, it has been reported that 20% of all hospital admissions among diabetic patients in the United States are for foot problems. (Reiber G E, et al., in Harris M I, et al, (eds): *Diabetes in America*. Washington, National Institute of Diabetes and Digestive and Kidney Diseases, 1995, pp 409–427). That such ulcerations may lead to lower extremity amputation (Parkhouse N, et al., *N Engl J Med* 1988;318:1306–1309) is borne out by the fact that the rate of lower limb amputation is fifteen times higher in diabetic versus non-diabetic patients (Veves A, et al., *Diabetes* 1998; 47:457–463). Even with intensive insulin therapy, as reported in the Diabetes Control and Complications Trial (DCCT), the incidence of new clinically detected neuropathy per patient per year was 3.1% in the non-retinopathy group and 7.0% in the group with baseline retinopathy; with conventional therapy, the incidence of neuropathy increased to 9.8% and 16.1% with and without retinopathy (The Diabetes Control and Complications Trial Research Group, *N Engl J Med* 1993;329:977–988). When loss of sensation is compounded by loss of control over blood flow due to autonomic neuropathy and lower extremity vascular obstruction, the threat of limb loss is exacerbated. In the case of peripheral artery disease, hospital mortality, length of hospitalization, and complications resulting from surgery are all increased in the presence of diabetes (Currie C J, et al., *Diabetes Care* 1998;21:42–48).

In view of the foregoing, a need still exists to better understand the molecular processes underlying peripheral neuropathy, and to develop improved drug therapies to replace or supplement the existing methods for treating peripheral neuropathies, particularly ischemic peripheral neuropathy. Preferably, such drug therapies would be designed to reduce or prevent nerve damage at its earliest stages and to enhance peripheral nerve repair following diagnosis and treatment.

SUMMARY OF THE INVENTION

The invention is based, in part, on the observation that a number of patients receiving angiogenic growth factor treatment for vascular insufficiency appeared to exhibit an improvement in sensory neuropathy. To test Applicant's hypothesis that the angiogenic growth factor either directly or indirectly improved the peripheral neuropathy, Applicant developed an animal model of hindlimb ischemia which exhibits severe peripheral neuropathy and which, in contrast to existing in vitro and in vivo methods, is predictive of an in vivo therapeutic effect of an agent for treating a peripheral neuropathy, administered (intramuscularly) to this animal model a vector containing a nucleic acid encoding VEGF ("VEGF vector"), and discovered that this angiogenic growth factor attenuated the development of ischemic peripheral neuropathy and enhanced the recovery of established ischemic peripheral neuropathy. Thus, Applicant describes herein newly discovered functions for VEGF and other angiogenic growth factors, namely, the ability to prevent or reduce ischemia induced nerve damage at its earliest stages and the ability to enhance peripheral nerve repair following the onset of peripheral neuropathy. Accordingly, the instant invention is directed to compositions and methods that are based upon the discovery of these newly-discovered functions for angiogenic growth factors. Exemplary conditions that are characterized by peripheral neuropathy include: (a) an ischemic peripheral neuropathy; (b) a neuropathy associated with a systemic condition; (c) a toxin-induced peripheral neuropathy; and (d) a genetically acquired peripheral neuropathy.

According to one aspect of the invention, a method for treating a condition characterized by peripheral neuropathy in a subject is provided. In certain preferred embodiments, the subject is otherwise free of symptoms calling for treatment with an angiogenic growth factor. The method involves administering at least one angiogenic growth factor (an "angiogenic growth factor nucleic acid" or an "angiogenic growth factor polypeptide") to a subject in need of such treatment in an amount effective to alleviate a symptom of peripheral neuropathy in the subject. The symptom of peripheral neuropathy can be one or more of the symptoms which are used by the skilled medial professional to diagnose a peripheral neuropathy.

Exemplary angiogenic growth factors (including all genes and isoforms of each gene product) for use in accordance with the methods of the invention include: vascular endothelial cell growth factor (VEGF), acidic fibroblast growth factor (aFGF), basic fibroblast growth factor (bFGF), epidermal growth factor, transforming growth factors α and β, platelet-derived endothelial growth factor, platelet-derived growth factor, tumor necrosis factor α, hepatocyte growth factor (scatter factor), erythropoietin, colony stimulating factor (CSF), macrophage-CSF (M-CSF), granulocyte/macrophage CSF (GM-CSF), angiopoietin 1 and 2, and nitric oxide synthase (NOS). The nucleic acid and amino acid sequences for these and other angiogenic growth factors are available in public databases such as GenBank and in the literature. The preferred angiogenic growth factor is VEGF, more preferably, a VEGF nucleic acid. In certain particularly preferred embodiments, the VEGF nucleic acid is administered to the subject in conjunction with a second angiogenic growth factor nucleic acid which, preferably, is bFGF. The compositions and methods of the invention are useful for replacing existing drug therapies, as well as for improving the effectiveness of existing therapies for treating conditions that are characterized by peripheral neuropathy. In general, such conditions are diagnosed by detecting one or a combination of motor, sensory, sensorimotor, or autonomic neural dysfunctions in the subject.

An "angiogenic growth factor" embraces an "angiogenic growth factor nucleic acid" and an "angiogenic growth factor polypeptide". As used herein, an "angiogenic growth factor polypeptide" refers to any protein, polypeptide, mutein or portion thereof that is capable of inducing endothelial cell growth. VEGF is a particularly preferred angiogenic growth factor (e.g., VEGF 1 (also referred to as VEGF A); VEGF 2 (also referred to as VEGF C); VEGF B; and VEGF D). An angiogenic growth factor nucleic acid refers to a nucleic acid which encodes an angiogenic growth factor polypeptide. The invention embraces the administration of angiogenic growth factor nucleic acids and polypeptides for the treatment of peripheral neuropathies. The invention also embraces agents that upregulate expression of an angiogenic growth factor polypeptide in vivo.

The complete coding sequence for representative preferred human angiogenic growth factors cDNA and predicted amino acid sequence are available in public databases such as GenBank and in literature. In particular, certain of the VEGF genes, isoforms, fragments, and analogs thereof that are useful for practicing the claimed invention are described in GenBank Accession Nos. NM 003376 ("*Homo sapiens* vascular endothelial growth factor (VEGF) mRNA"); NM 003377 ("*Homo sapiens* vascular endothelial growth factor B (VEGFB) mRNA"); NM 005429 ("*Homo sapiens* vascular endothelial growth factor C (VEGFC) mRNA"); NM 004469 ("*Homo sapiens* c-fos induced growth factor (vascular endothelial growth factor D) (FIGF) mRNA); AF 024710 ("*Homo sapiens* vascular growth factor (VEGF (165)) mRNA, 3'UTR, mRNA sequence"); and U.S. Pat. No. 6,013,780 ("$VEGF_{145}$ expression vectors"); U.S. Pat. No. 5,935,820 ("Polynucleotides encoding vascular endothelial growth factor 2"); U.S. Pat. No. 5,607,918 ("Vascular endothelial growth factor-B and DNA coding therefor"); and U.S. Pat. No. 5,219,739 ("DNA sequences encoding bVEGF 120 and hVEGF 121 and methods for the production of bovine and human vascular endothelial cell growth factors, $bVEGF_{120}$ and $hVEGF_{121}$"), including references cited therein, the entire contents of the foregoing accession numbers, patent documents, and references are incorporated in their entirety by reference.

The preferred angiogenic growth factor nucleic acids of the invention encode the above-identified angiogenic growth factor polypeptides, as well as their homologs and alleles and functionally equivalent fragments or variants of the foregoing. For example, human VEGF 1 (VEGF A) exists in four principal isoforms, $phVEGF_{121}$; $phVEGF_{145}$; $phVEGF_{165}$; and $phVEGF_{189}$. Preferably, the angiogenic growth factor nucleic acid has the nucleotide sequence encoding an intact human angiogenic growth factor polypeptide, i.e., the complete coding sequence of the gene encoding a human angiogenic growth factor; however the invention also embraces the use of nucleic acids encoding fragments of an intact angiogenic growth factor.

In general, the angiogenic growth factor nucleic acid is operatively coupled to a promoter that can express the angiogenic growth factor in a targeted cell (e.g., an endothelial cell, a nerve cell, a muscle cell). Optionally, the nucleic acid is contained in an appropriate expression vector (e.g., plasmid, adenoviral vector, modified adenoviral vector, retroviral vector, liposome) to more efficiently genetically modify the targeted cell and achieve expression of the angiogenic growth factor.

According to another aspect of the invention, an alternative method for treating a condition characterized by peripheral neuropathy in a subject is provided. The method involves: administering at least one angiogenic growth factor to a subject in need of such treatment in an amount and for a period of time effective to alleviate a symptom of peripheral neuropathy in the subject. The symptom of peripheral neuropathy can be one or more of the symptoms which are used by the skilled medical professional to diagnose a peripheral neuropathy. The period of time that is effective for alleviating a symptom of peripheral neuropathy is significantly greater than the period of time during which an angiogenic growth factor typically is administered to a subject for the purpose of revascularization in an ischemic tissue. In general, angiogenic growth factors are administered to a patient for a period of up to, and including, about twelve weeks to enhance blood vessel development in ischemic tissue. In contrast, in the preferred embodiments of this aspect of the invention, administration of the angiogenic growth factor is for greater than twelve weeks; more preferably, greater than eighteen weeks; and most preferably, greater than about twenty-four weeks. In some instances, treatment for the purposes of this aspect of the invention is continued for at least six months to several years, and more preferably, from six months to one, two, three years or for the patient's lifetime in the case of chronic peripheral neuropathy.

According to yet another aspect of the invention, a further method for treating a condition characterized by peripheral neuropathy in a subject is provided. The method involves administering at least one angiogenic growth factor to a subject in need of such treatment in an amount effective to alleviate a symptom of peripheral neuropathy in the subject, wherein administering is by intramuscular injection into a tissue at an injection site that is proximate to a nerve which is suspected of a neuropathy and that is distal to an injection site that would be selected for the purpose of revascularization (e.g., neovascularization). In general, intramuscular injection into a tissue for the purpose of revascularization in ischemic tissue is accomplished by localized delivery of the angiogenic growth factor to the site of a vascular blockage. In contrast, according to the embodiments in which a subject also presents with a vascular insufficiency, intramuscular injection of angiogenic growth factors, preferably, is into the tissue at a location which excludes these locations. The preferred locations into which the angiogenic factors are intramuscularly injected for the purpose of treating peripheral neuropathy include sites which are proximate to a nerve which is suspected of a neuropathy. An amount of the angiogenic growth factor is administered to alleviate a symptom of a peripheral neuropathy. The symptom of peripheral neuropathy can be one or more symptoms which are used by the skilled medical professional to diagnose a peripheral neuropathy.

According to yet another aspect of the invention, a method for treating a subject who has sustained a peripheral nerve injury is provided. The method involves administering at least one angiogenic growth factor to a subject in need of such treatment in an amount effective to enhance peripheral nerve regeneration. Preferably, the subject is otherwise free of symptoms calling for treatment with an angiogenic growth factor. The angiogenic growth factor nucleic acids and polypeptides and exemplary conditions which are characterized by peripheral neuropathy are as described above.

It is to be understood that an angiogenic growth factor polypeptide can be used in place of an angiogenic growth factor nucleic acid in treating any of the foregoing conditions. Thus, according to still another aspect of the invention, pharmaceutical preparations are provided that contain an angiogenic growth factor nucleic acid or an angiogenic growth factor polypeptide. The pharmaceutical preparations contain the above-described angiogenic growth factors, together with a pharmaceutically-acceptable carrier. Preferably, the angiogenic growth factors are present in the compositions in an amount effective for treating a peripheral neuropathy. The angiogenic growth factors are particularly useful for the treatment of ischemic peripheral neuropathy. Preferably, this amount is sufficient to enhance nerve regeneration in vivo.

According to still another aspect of the invention, the above angiogenic growth factors (angiogenic growth factor nucleic acids and angiogenic growth factor polypeptides), alone or in combination, are used in the preparation of medicaments for the treatment of a peripheral neuropathy. The method involves placing the angiogenic growth factor(s) in a pharmaceutically-acceptable carrier. The preferred angiogenic growth factors are as described above.

It is noteworthy that in certain embodiments, the preferred subjects treated according to the methods set forth above are otherwise free of symptoms calling for angiogenic growth factor treatment, either by administration of the angiogenic growth factor polypeptide or by an angiogenic growth factor nucleic acid. Thus, in certain select embodiments, the subjects are not otherwise being treated using a gene therapy protocol or, if being treated using gene therapy, the protocol for the methods of the invention differ in the dosage or duration of treatment (greater than about twelve weeks) and/or the site of intramuscular injection (in the proximity of a nerve suspected of a neuropathy).

The invention also contemplates the use of angiogenic growth factors in experimental model systems to determine the role that angiogenic growth factors play in the repair of peripheral nerves or in mediating an adverse health consequence occurring as a result of peripheral neuropathy. An ischemic animal model of peripheral neuropathy is described in the Examples and can be used to select agents for treatment of this condition. The agent (e.g., an angiogenic growth factor as described above) is administered to the animal, locally or systemically, and the animal's response is monitored and compared to control animals that do not receive the angiogenic growth factors. In this manner, additional agents which are useful for treating peripheral neuropathies can be identified.

These and other aspects of the invention will be described in greater detail below. Throughout this disclosure, all technical and scientific terms have the same meaning as commonly understood by one of ordinary skill in the art to which this invention pertains unless defined otherwise.

DETAILED DESCRIPTION OF THE DRAWINGS

Figure 1B:
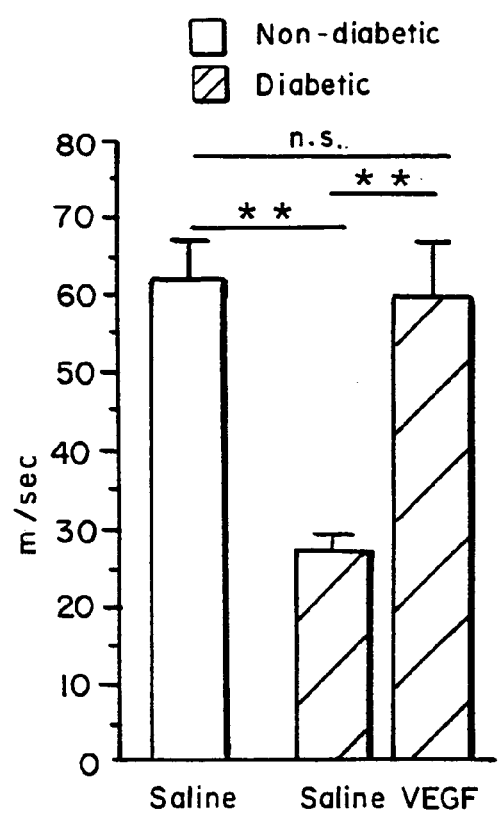

FIG. 1A shows the motor nerve conduction velocity for non-diabetic and diabetic animals which received saline or VEGF; and FIG. 1B shows sensory nerve conduction velocity for non-diabetic and diabetic animals which received saline and VEGF.

This application, particularly the Examples, may refer to Figures; however, none of the figures are essential for enablement of the invention.

DETAILED DESCRIPTION OF THE INVENTION

The invention is based, in part, on the observation that a number of patients receiving an angiogenic growth factor to treat a vascular insufficiency appeared to exhibit an improvement in sensory neuropathy. Accordingly, Applicant hypothesized that the angiogenic growth factor either directly or indirectly improved the peripheral neuropathy. To test this hypothesis, Applicant developed an animal model of hindlimb ischemia which exhibits severe peripheral neuropathy and which resembles and is predictive of a human peripheral neuropathy. Applicant then administered (intramuscularly) to the animal model, a vector containing a nucleic acid encoding VEGF ("VEGF vector"), and discovered that this angiogenic growth factor attenuated the development of ischemic peripheral neuropathy and enhanced the recovery of established ischemic peripheral neuropathy. Based on these discoveries, Applicant describes herein new functions for VEGF and other angiogenic growth factors, namely, the ability to prevent or reduce ischemia induced nerve damage at its earliest stages as well as the ability to enhance peripheral nerve repair. Accordingly, the instant invention is directed to compositions and methods that are based upon the discovery of these newly-discovered functions for angiogenic growth factors.

As used herein, "peripheral neuropathy" refers to a disorder affecting a segment of the peripheral nervous system. The invention involves using an angiogenic growth factor to reduce a neuropathology including, but not limited to, a distal sensorimotor neuropathy, or an autonomic neuropathy such as reduced motility of the gastrointestinal tract or atony of the urinary bladder. Preferred neuropathies that can be treated with the angiogenic growth factors of the invention also include neuropathies associated with ischemic disease, neuropathies associated with a systemic disease, e.g., post-polio syndrome; genetically acquired neuropathies, e.g., Charcot-Marie-Tooth disease; and neuropathies caused by a toxic agent, e.g., a chemotherapeutic agent, such as vincristine. Each of these categories of conditions is discussed in more detail below.

According to one aspect of the invention, a method for treating a condition characterized by peripheral neuropathy in a subject is provided. The method involves administering at least one angiogenic growth factor (an "angiogenic growth factor nucleic acid" or an "angiogenic growth factor polypeptide") to a subject in need of such treatment in an amount effective to alleviate a symptom of peripheral neuropathy in the subject. The symptom of peripheral neuropathy can be one or more of the symptoms which are used by the skilled medical professional to diagnose a peripheral neuropathy. Exemplary angiogenic growth factors for use in accordance with the methods of the invention are described below. The nucleic acid and amino acid sequences for these and other angiogenic growth factors are available in public databases such as GenBank and in the literature. Preferably, the subject is otherwise free of symptoms calling for treatment with an angiogenic growth factor.

According to another aspect of the invention, an alternative method for treating a condition characterized by peripheral neuropathy in a subject is provided. The method involves: administering at least one angiogenic growth factor to a subject in need of such treatment in an amount and for a period of time effective to alleviate a symptom of peripheral neuropathy in the subject. The symptom of peripheral neuropathy can be one or more of the symptoms which are used by the skilled medical professional to diagnose a peripheral neuropathy. The period of time that is effective for alleviating a symptom of peripheral neuropathy is significantly greater than the period of time during which an angiogenic growth factor is administered to a subject for the purpose of revascularization of an ischemic tissue. Typically, angiogenic growth factors are administered to a patient for a period of up to, and including, about twelve weeks for enhancing blood vessel development in ischemic vascular tissue. In contrast, in the preferred embodiments of this aspect of the invention, administration of the angiogenic growth factor is for greater than about twelve weeks; more preferably, greater than eighteen weeks; and most preferably, greater than about twenty-four weeks. In some instances, treatment for the purposes of this aspect of the invention is continued for at least six months to several years, and more preferably, from six months to one, two, three years, or for the patient's lifetime in the case of chronic peripheral neuropathy. Repeated injections using controlled release microparticles containing the angiogenic growth factors can be used for this purpose.

According to yet another aspect of the invention, a further method for treating a condition characterized by peripheral neuropathy in a subject is provided. The method involves administering at least one angiogenic growth factor to a subject in need of such treatment in an amount effective to alleviate a symptom of peripheral neuropathy in the subject, wherein administering is by intramuscular injection into a tissue at an injection site that is proximate to a nerve which is suspected of a neuropathy and that is distal to an injection site that would be selected for the purpose of revascularization (e.g., neovascularization) in an ischemic tissue. In general, intramuscular injection into a tissue for the purpose of revascularization in ischemic tissue is accomplished by localized delivery of the angiogenic growth factor to the site of a vascular blockage. In contrast, according to the embodiments in which a subject also presents with a vascular insufficiency, intramuscular injection of angiogenic growth factors, preferably, is into a tissue at a location which excludes these locations. The locations into which the angiogenic factors are intramuscularly injected for the purpose of treating peripheral neuropathy include muscle which is proximate to a nerve which is suspected of a neuropathy.

According to yet another aspect of the invention, a method for treating a subject who has sustained a peripheral nerve injury is provided. The method involves administering at least one angiogenic growth factor to a subject in need of such treatment in an amount effective to enhance peripheral nerve regeneration. Preferably, the subject is otherwise free of symptoms calling for treatment with an angiogenic growth factor.

As used herein, an "angiogenic growth factor" embraces an "angiogenic growth factor nucleic acid" and an "angiogenic growth factor polypeptide". An "angiogenic growth factor polypeptide" refers to any protein, polypeptide, mutein or portion that is capable of inducing endothelial cell growth. VEGF is a particularly preferred angiogenic growth factor. An angiogenic growth factor nucleic acid refers to a nucleic acid which encodes an angiogenic growth factor. The invention embraces the administration of nucleic acids or polypeptides for the treatment of peripheral neuropathies.

Homologs and alleles of the nucleic acid and amino acid sequences reported for the angiogenic growth factors, such as those identified herein, also are embraced within the definition of an "angiogenic growth factor". In addition, the angiogenic growth factor nucleic acids of the invention include nucleic acids which code for the angiogenic growth factor polypeptides having the sequences reported in the public databases and/or literature, but which differ from the naturally occurring nucleic acid sequences in codon sequence due to the degeneracy of the genetic code. The invention also embraces isolated functionally equivalent fragments, variants, and analogs of the foregoing nucleic acids; proteins and peptides coded for by any of the foregoing nucleic acids; and complements of the foregoing nucleic acids. Particularly preferred fragments of the VEGF nucleic acid and VEGF polypeptides are identified below.

The angiogenic growth factor nucleic acid may be any nucleic acid (DNA or RNA) including genomic DNA, cDNA and mRNA, encoding an angiogenic growth factor which can be used to express a growth factor, e.g., a protein, polypeptide, mutein or portion thereof, that is capable of inducing either directly or indirectly, the formation of new blood vessels (Folkman, et al., Science, 235:442–447 (1987)). These include, for example, vascular endothelial growth factor (VEGF), acidic fibroblast growth factor (aFGF) (Bjornsson, et al., Proc. Natl. Acad. Sci. USA, 88:8651–8655, (1991)), basic fibroblast growth factor (bFGF) (Schwarz, et al., J. Vasc Surg., 5:280–288, (1987)), epidermal growth factor (EGF), transforming growth factors α and β (TGF-α and TGF-β), platelet-derived endothelial cell growth factor (PD-ECGF), platelet-derived growth factor (PDGF) itself, tumor necrosis factor α (TNF-α), hepatocyte growth factor (HGF), erythropoietin, colony stimulating factor (CSF), macrophage-CSF (M-CSF), granulocyte/macrophage CSF (GM-CSF) and nitric oxide synthase (NOS). See, Klagsbrun, et al., Annu. Rev. Physiol., 53:217–239 (1991); Folkman, et al., J. Biol. Chem., 267: 10931–10934 (1992) and Symes, et al., Current Opinion in Lipidology, 5:305–312 (1994). Muteins or fragments of an angiogenic growth factor may be used provided they induce nerve regeneration or alleviate a symptom of peripheral neuropathy.

The feasibility of using recombinant formulations of angiogenic growth factors to expedite and/or augment collateral artery development in animal models of myocardial and hindlimb ischemia has been reported. See, Baffour, et al., supra (bFGF); Pu, et al., Circulation, 88:208–215 (1993)

(aFGF); Yanagisawa-Miwa, et al., supra (bFGF); Ferrara, et al., Biochem. Biophys. Res. Commun., 161:851–855 (1989) (VEGF). In addition, therapeutic angiogenesis has been reported in the same or closely related models following administration of recombinant endothelial cell growth factor (ECGF) (Pu, et. al., Circulation, 88:208–215 (1993)) and VEGF (Takeshita, et al., Circulation, 90:228–234 (1994) supra). Previous studies, employing the animal model of chronic limb ischemia, reported an efficacy of intramuscular endothelial cell growth factor (ECGF) (Pu, et al., Circulation, 88:208–215 (1993) or VEGF (Takeshita, et al., Circulation, 90:228–234 (1994) supra) administration. None of these references have suggested a role for angiogenic growth factors for treating peripheral neuropathy.

VEGF is a particularly preferred angiogenic growth factor. Any of the VEGF isoforms (e.g., VEGF 1, 2, 3, 4, and 5) may be used in accordance with the methods of the invention. VEGF reportedly is an endothelial cell-specific mitogen (Ferrara, et al., Biochem Biophys Res Commun., 161:851–855, (1989), Keck, et al., Science, 246:1309–1312 (1989), and Plouet, et al., Embo J., 3801–3806 (1989)). VEGF was purified independently as a tumor-secreted factor that included vascular permeability by the Miles assay (Keck, et al., supra, and Connolly, et al., J. Biol. Chem., 264:20017–20024 (1989), and thus has an alternate designation, vascular permeability factor (VPF). Two features distinguish VEGF from other heparin-binding, angiogenic growth factors. First, the $NH_2$ terminus of VEGF is preceded by a typical signal sequence; therefore, unlike bFGF, VEGF can be secreted by intact cells. Second, its high-affinity binding sites, shown to include the tyrosine kinase receptors Flt-1 and Flt-1/KDR are present on endothelial cells. Ferrara, et al., supra, and Conn, et al., Proc. Natl. Acad. Sci. USA, 87:1323–1327 (1990). DNA encoding VEGF is disclosed in U.S. Pat. No. 5,332,671, the disclosure of which is herein incorporated by reference.

Preferably, the angiogenic growth factor contains a secretory signal sequence that facilitates secretion of the protein. Angiogenic growth factors having native signal sequences, e.g., VEGF, are preferred. Angiogenic growth factors that do not have native signal sequences, e.g., bFGF, can be modified to contain such sequences using routine genetic manipulation techniques. See, Nabel, et al., Nature, 362:844 (1993).

The nucleotide sequence of numerous peptides and proteins, including the angiogenic growth factors, are readily available through a number of computer data bases, for example, GenBank, EMBL and Swiss-Prot. Using this information, a DNA or RNA segment encoding the desired may be chemically synthesized or, alternatively, such a DNA or RNA segment may be obtained using routine procedures in the art, e.g, PCR amplification.

To simplify the manipulation and handling of the nucleic acid encoding the growth factor, the nucleic acid preferably is inserted into a cassette where it is operably linked to a promoter. The promoter must be capable of driving expression of the mitogen in the desired target host cell, e.g., an endothelial cell, a muscle cell, a nerve cell. The selection of appropriate promoters can readily be accomplished. Preferably, a high expression promoter is used. An example of a suitable promoter is the 763-base-pair cytomegalovirus (CMV) promoter. The Rous sarcoma virus (RSV) (Davis, et al., Hum Gene Ther 4:151 (1993)) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). A plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/122618.

If desired, the DNA may also be used with a micro delivery vehicle such as cationic liposomes and adenoviral vectors. For a review of the procedures for liposome preparation, targeting and delivery of contents, see Mannino and Gould-Fogerite, Bio Techniques, 6:682 (1988). See also, Feigner and Holm, Bethesda Res. Lab. Focus, 11 (2):21 (1989) and Maurer, R. A., Bethesda Res. Lab. Focus, 11(2): 25 (1989).

Replication-defective recombinant adenoviral vectors, can be produced in accordance with known techniques. See, Quantin, et al., Proc. Natl. Acad. Sci. USA, 89:2581–2584 (1992); Stratford-Perricadet, et al., J. Clin. Invest., 90:626–630 (1992); and Rosenfeld, et al., Cell, 68:143–155 (1992).

In certain situations, it may be desirable to use nucleic acids encoding two or more different proteins in order to optimize the therapeutic outcome. For example, DNA encoding two angiogenic growth factors, e.g., VEGF and bFGF, can be used to provide an improved treatment over the use of bFGF alone. Alternatively, an angiogenic growth factor nucleic acid can be combined with other genes or their encoded gene products to enhance the activity of targeted cells, while simultaneously inducing angiogenesis, if desired, including, for example, nitric oxide synthase, L-arginine, fibronectin, urokinase, plasminogen activator and heparin.

In order to facilitate injection, the nucleic acid is formulated with a pharmaceutically acceptable carrier. Examples of suitable carriers include, saline, albumin, dextrose and sterile water. The nucleic acid is injected into the ischemic tissue using standard injection techniques by use of, for example, a hypodermic needle. Hypodermic needle sizes from no. 29 to no. 16 are preferred. The nucleic acid may also be injected by an externally applied local injection apparatus, such as that used to inject antigens for allergy testing; or a transcutaneous "patch" capable of delivery to subcutaneous muscle. In general, the effective dose of the nucleic acid will be a function of the particular expressed protein, the target tissue, the patient and his or her clinical condition. Effective amounts of DNA typically are between about 1 and 4000 μg, more preferably from about 1000 to 4000 μg and, most preferably, from about 2000 to 4000 μg.

Once injected, the nucleic acid capable of expressing the desired angiogenic growth factor is taken up and expressed by the cells of the tissue. Because the vectors containing the nucleic acid of interest are not normally incorporated into the genome of the cells, expression of the protein of interest takes place for only a limited time. Typically, the angiogenic growth factor is expressed at therapeutic levels for about two days to several weeks, preferably for about 1–2 weeks. Reinjection of the DNA can be utilized to provide additional periods of expression of the angiogenic growth factor. If desired, a retrovirus vector can be used to incorporate the heterologous DNA into the genome of the cells and, thereby, increase the length of time during which the therapeutic polypeptide is expressed, from several weeks to indefinitely.

The invention is not limited to treatment of ischemic tissue, but rather, is useful for treating peripheral neuropathies of various origin. Exemplary conditions that are characterized by peripheral neuropathy are known to those of ordinary skill in the art and include, but are not limited to, the following categories of disorders: (a) ischemic peripheral neuropathies; (b) toxin-induced peripheral neuropathies; (c) neuropathies associated with systemic disease; and (d) genetically acquired peripheral neuropathies.

Exemplary ischemic peripheral neuropathies include neuropathies associated with ischemic tissues such as those associated with a diabetic condition, peripheral vascular disease, or other vascular insufficiency.

Exemplary toxin-induced peripheral neuropathies are described in U.S. Pat. No. 5,648,335, entitled "Prevention and treatment of peripheral neuropathy", issued to Lewis, et al., and include neuropathies that are caused by neurotoxic agents including, therapeutic drugs, antineoplastic agents, contaminants in foods or medicinals, and environmental and industrial pollutants. By "toxic agent", or neurotoxic agent, is meant a substance that through its chemical action injures, impairs, or inhibits the activity of a component of the nervous system. The list of neurotoxic agents that cause neuropathies is lengthy, and includes, but is not limited to, neoplastic agents such as vincristine, vinblastine, cisplatin, taxol, or dideoxy-compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillin or chloramphenicol, or megadoses of vitamins A, D, or $B_6$. An extensive, although not complete, list of chemical compounds with neurotoxic side-effects is found in Table 1. Although this list provides examples of neurotoxic compounds, it is intended to exemplify, not limit, the scope of the invention. Other toxic agents can cause neuropathies, and can be characterized by methods known to one skilled in the art. By "exposure to a toxic agent" is meant that the toxic agent is made available to, or comes into contact with, a mammal of the invention. Exposure to a toxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

TABLE 1

AGENTS THAT CAUSE PERIPHERAL NEUROPATHY

| AGENT | ACTIVITY |
|---|---|
| Acetazolamide | diuretic |
| Acrylimide | flocculent, grouting agent |
| Adriamycin | antineoplastic |
| alcohol (ethanol) solvent | recreational drug |
| Almitrine | respiratory stimulant |
| Amiodarone | antiarrhythmic |
| Amphotericin | antimicrobial |
| Arsenic | herbicide, insecticide |
| Aurothioglucose | antirheumatic |
| Barbiturates | anticonvulsant, sedative |
| Buckthorn | toxic berry |
| Carbamates | insecticide |
| carbon disulfide ($CS_2$) | industrial |
| chloramphenicol | antibacterial |
| chloroquine | antimalarial |
| cholestyramine | antihyperlipoproteinemic |
| cisplatin | antineoplastic |
| clioquinol amebicide | antibacterial |
| colestipol | antihyperlipoproteinemic |
| colchicine | gout suppressant |

TABLE 1-continued

AGENTS THAT CAUSE PERIPHERAL NEUROPATHY

| AGENT | ACTIVITY |
|---|---|
| colistin | antimicrobial |
| cycloserine | antibacterial |
| cytarabine | antineoplastic |
| dapsone | dermatologic including leprosy |
| dideoxycytidine | antineoplastic |
| dideoxyinosine | antineoplastic |
| dideoxythymidine | antiviral |
| disulfiram | antialcohol |
| doxorubicin | antineoplastic |
| ethambutol | antibacterial |
| ethionamide | antibacterial |
| glutethimide | sedative, hypnotic |
| gold | antirheumatic |
| hexacarbons solvents | hormonal contraceptives |
| hexamethylolmelamine | fireproofing, creaseproofing |
| hydralazine | antihypertensive |
| hydroxychloroquine | antirheumatic |
| imipramine | antidepressant |
| indomethacin | anti-inflammatory |
| inorganic lead | toxic metal in paint, etc. |
| isoniazid | antituberculous |
| lithium | antidepressant |
| methylmercury | industrial waste |
| metformin | antidiabetic |
| methylhydrazine | synthetic intermediate |
| metronidazole | antiprotozoal |
| misonidazole | radiosensitizer |
| nitrofurantoin | urinary antiseptic |
| nitrogen mustard antineoplastic | nerve gas |
| nitrous oxide | anesthetic |
| organophosphates | insecticides |
| ospolot | anticonvulsant |
| penicillin | antibacterial |
| perhexiline | antiarrhythmic |
| perhexiline maleate | antiarrhythmic |
| phenytoin | anticonvulsant |
| platinum | drug component |
| primidone | anticonvulsant |
| procarbazine | antineoplastic |
| pyridoxine | vitamin B6 |
| sodium cyanate | anti-sickling |
| streptomycin | antimicrobial |
| sulphonamides | antimicrobial |
| suramin | antineoplastic |
| tamoxifen | antineoplastic |
| taxol | antineoplastic |
| thalidomide | antileprous |
| thallium | rat poison |
| triamterene | diuretic |
| trimethyltin | toxic metal |
| L-tryptophan | health food additive |
| vincristine | antineoplastic |
| vinblastine | antineoplastic |
| vindesine | antineoplastic |
| vitamin A | mega doses |
| vitamin D | mega doses |

In general, neurotoxicity is dose-related, and presents as reduced intestinal motility and peripheral neuropathy, especially in the distal muscles of the hands and feet, postural hypotension, and atony of the urinary bladder. Similar problems have been reported with taxol and cisplatin (Mollman, J. E., 1990, New Eng Jour Med. 322:126–127), although cisplatin-related neurotoxicity reportedly can be alleviated with nerve growth factor (NGF) (Apfel, S. C. et al, 1992, Annals of Neurology 31:76–80). Although the neurotoxicity is sometimes reversible after removal of the neurotoxic agent, recovery reportedly can be a very slow process (Legha, S., 1986, Medical Toxicology 1:421–427; Olesen, et al., 1991, Drug Safety 6:302–314).

Exemplary neuropathies associated with a systemic condition include: uremia, childhood cholestatic liver disease, chronic respiratory insufficiency, alcoholic polyneuropathy, multiple organ failure, sepsis, hypoalbuminemia, eosinophilia-myalgia syndrome, hepatitis, porphyria, hypoglycemia, vitamin deficiency, chronic liver disease, primary biliary cirrhosis, hyperlipidemia, leprosy, Lyme disease, herpes zoster, Guillain-Barre syndrome, chronic inflammatory demyelinating polyradiculoneuropathy, sensory perineuritis, acquired immunodeficiency syndrome (AIDS)-associated neuropathy, Sjogren's syndrome, primary vasculitis (such as polyarteritis nodosa), allergic granulomatous angiitis (Churg-Strauss), hypersensitivity angiitis, Wegener's granulomatosis, rheumatoid arthritis, systemic lupus erythematosis, mixed connective tissue disease, scleroderma, sarcoidosis, vasculitis, systemic vasculitides, acute inflammatory demyelinating polyneuropathy, post-polio syndrome, carpal tunnel syndrome, pandysautonomia, primary systemic amyloidosis, hypothyroidism, chronic obstructive pulmonary disease, acromegaly, malabsorption (sprue, celiac disease), carcinomas (sensory, sensorimotor, late and demyelinating), lymphoma (including Hodgkin's), polycythemia vera, multiple myeloma (lytic type, osteosclerotic, or solitary plasmacytoma), benign monoclonal gammopathy, macroglobulinemia, and cryoglobulinemia.

Exemplary genetically acquired neuropathies include: peroneal muscular atrophy (Charcot-Marie-Tooth Disease, types I, II, and X), hereditary amyloid neuropathies, hereditary sensory neuropathy (type I and type II), porphyric neuropathy, hereditary liability to pressure palsy, Fabry's disease, adrenomyeloneuropathy, Riley-Day syndrome, Dejerine-Sottas neuropathy (hereditary motor-sensory neuropathy-III), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia. Also included in the invention are mononeuropathy multiplex, plexopathy, and pure motor neuropathy.

The angiogenic growth factors of the invention are administered in effective amounts. An effective amount is a dosage of the angiogenic growth factor nucleic acid sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the healthcare practitioner. For example, in connection with peripheral neuropathy, an effective amount is that amount which alleviates a symptom of the neuropathy. Likewise, an effective amount for treating a subject who has sustained a peripheral nerve injury, would be an amount sufficient to enhance peripheral nerve regeneration. Thus, it will be understood that the angiogenic growth factor of the invention can be used to treat the above-noted conditions prophylactically in subjects at risk of developing the foregoing conditions. As used herein, "treat" embraces all of the foregoing. It is preferred generally that a maximum dose be used, that is, the highest safe dose according to sound medical judgment.

A particularly important aspect of the invention involves the use of the angiogenic growth factors of the invention for treating subjects who have sustained a peripheral neuropathy as a side effect of ischemic heart disease. Ischemia refers to a lack of oxygen due to inadequate perfusion of blood. Ischemic heart disease is characterized by a disturbance in cardiac function due to an inadequate supply of oxygen to the heart. The most common form of this disease involves a reduction in the lumen of coronary arteries, which limits coronary blood-flow.

When ischemic heart disease becomes very serious, management of the disease becomes invasive. Until recently, ischemic heart disease was treated by coronary-artery, bypass surgery. Less invasive procedures, however, now have been developed. These procedures involve the use of catheters introduced into the narrowed region of the blood vessel ("the stenosis") for mechanically disrupting, laser ablating or dilating the stenosis. The most widely used method to achieve revascularization of a coronary artery is percutaneous transluminal coronary angioplasty. A flexible guide wire is advanced into a coronary artery and positioned across the stenosis. A balloon catheter then is advanced over the guide wire until the balloon is positioned across the stenosis. The balloon then is repeatedly inflated until the stenosis is substantially eliminated. This procedure, as compared to heart surgery, is relatively noninvasive and typically involves a hospital stay of only a few days. The procedure is an important tool in the management of serious heart conditions and can also be used to deliver the angiogenic growth factor of the invention to a local site of ischemic tissue and for treatment of a neuropathy in the ischemic tissue. Alternatively, the angiogenic growth factors can be intramuscularly injected directly into the ischemic tissue. In certain embodiments, the angiogenic growth factors are in the form of controlled release preparations for the sustained delivery of the factors to the ischemic or other tissue that presents symptoms of a peripheral neuropathy. Controlled release systems for delivery of an angiogenic growth factor nucleic acid or polypeptide are described in more detail below.

A subject, as used herein, refers to any mammal (preferably, a human) that may be susceptible to a condition associated with peripheral neuropathy (such as the conditions described above). In certain embodiments, the mammal is otherwise free of symptoms calling for angiogenic growth factor treatment. Different aspects of the invention may exclude one or more of the following subject populations that present with a peripheral neuropathy: (1) patients presenting with a vascular disease; (2) patients presenting with a vascular obstruction (large vessels); (3) patients presenting with a microvascular disease; (4) patients presenting with an ischemic tissue, such as an ischemic limb; (5) patients being treated with an angiogenic growth factor to promote revascularization; and (6) patients who are being treated using gene therapy.

In some particular embodiments, the preferred vehicle is a biocompatible micro particle or implant that is suitable for implantation into the subject. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promotor. The polymeric matrix is used to achieve sustained release of the exogenous gene in the subject. In accordance with the instant invention, the angiogenic growth factor nucleic acids described herein are encapsulated or dispersed within the biocompatible, preferably biodegradable polymeric matrix disclosed in PCT/US/03307. The polymeric matrix preferably is in the form of a micro particle such as a micro sphere (wherein the angiogenic growth factor nucleic acid is dispersed throughout a solid polymeric matrix) or a microcapsule (wherein the angiogenic growth factor nucleic acid is stored in the core of a polymeric shell). Other forms of the polymeric matrix for containing the angiogenic growth factor nucleic acid include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver the angiogenic growth factor nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the angiogenic growth factor nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly (ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described angiogenic growth factors for use as a medicament, methods for preparing the medicament and methods for the sustained release of the medicament in vivo. In the preferred embodiments, the angiogenic growth factor nucleic acid is a human VEGF nucleic acid, alone or in combination with a human bFGF nucleic acid. Preferably, the angiogenic growth factor nucleic acid is operably linked to a gene expression sequence to permit expression of the angiogenic growth factor nucleic acid in the target cell.

Compaction agents also can be used alone, or in combination with, a vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the isolated angiogenic growth factor nucleic acid in a form that is more efficiently taken up by the cell or, more preferably, in combination with one or more of the above-described vectors.

Other exemplary compositions that can be used to facilitate uptake by a target cell of the angiogenic growth factor nucleic acids include calcium phosphate and other chemical mediators of intracellular transport, microinjection compositions, electroporation and homologous recombination compositions (e.g., for integrating an angiogenic growth factor nucleic acid into a preselected location within the target cell chromosome).

The angiogenic growth factor nucleic acids code for an angiogenic growth factor polypeptide. As used herein, a "angiogenic growth factor polypeptide" refers to a polypeptide that, either directly or indirectly, enhances endothelial cell growth. Angiogenic growth factor polypeptides are useful for alleviating a symptom of peripheral neuropathy and/or enhancing nerve regeneration. The preferred angiogenic growth factor polypeptides of the invention are the human VEGF isoforms, administered alone or in combination with human bFGF. Angiogenic growth factor polypeptides further embrace functionally equivalent variants, and analogs of angiogenic growth factors, provided that the fragments, variants, and analogs alleviate a symptom of a peripheral neuropathy and/or enhance nerve regeneration. The invention also embraces proteins and peptides coded for by any of the foregoing angiogenic growth factor nucleic acids. The invention also embraces agents that upregulate expression of an angiogenic growth factor polypeptide in vivo.

A "functionally equivalent variant" of an angiogenic growth factor is capable of alleviating a symptom of a peripheral neuropathy and/or enhancing nerve regeneration in vitro or in vivo. An in vitro assay or an in vivo animal model (see, e.g., the Examples) can be used as a screening assay to measure the ability of a polypeptide to alleviate a symptom of a peripheral neuropathy and/or enhance nerve regeneration. The animal model disclosed in the Examples can be used to screen therapeutic drugs because it is predictive of the ability of the polypeptide to treat a peripheral neuropathy in vivo. Exemplary "functionally equivalent variants" of the angiogenic growth factors (such as the exemplary growth factors disclosed herein) include fragments of these factors, as well as polypeptide analogs of these factors which contain conservative amino acid substitutions, provided that the polypeptide variants and analogs are capable of alleviating a symptom of a peripheral neuropathy and/or enhancing nerve regeneration.

It will be appreciated by those skilled in the art that various modifications of the angiogenic growth factor polypeptide having the sequences deposited in the publicly available databases or functionally equivalent fragments thereof can be made without departing from the essential nature of the invention. Accordingly, it is intended that polypeptides which have the published amino acid sequences but which include conservative substitutions are embraced within the instant invention. As used herein, "conservative amino acid substitution" refers to an amino acid substitution which does not alter the relative charge or size characteristics of the polypeptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D. Fusion proteins, in which a peptide of the invention is coupled to a solid support (such as a polymeric bead for controlled release), or a reporter group (such as radiolabel or other tag), also are embraced within the invention.

When used therapeutically, the isolated angiogenic growth factors of the invention are administered in therapeutically effective amounts. In general, a therapeutically effective amount means that amount necessary to delay the onset of, inhibit the progression of, or halt altogether the particular condition being treated. As noted above, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount can vary throughout a broad dosage range, e.g., from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. In certain aspects of the invention described above, the angiogenic growth factors are administered over a period of months to years in the case of a chronic peripheral neuropathy.

The therapeutically effective amount of the isolated angiogenic growth factor is that amount effective to inhibit the development of peripheral neuropathy, alleviate a symptom of a peripheral neuropathy, and/or enhance nerve regeneration as determined by, for example, standard tests known in the art. It is believed that the angiogenic growth factors directly and/or indirectly enhance nerve regeneration in the vicinity of the target cell. Diagnostic tests that are used to diagnose a peripheral neuropathy can by used to select an effective amount of the angiogenic growth factor. In vitro assays are available to determine whether a factor has been effective in inducing nerve regeneration.

Optionally, the isolated angiogenic growth factor is administered to the subject in combination with an alternative method for treating the neuropathy or for treating the particular condition that is associated with the peripheral neuropathy. See, e.g., Harrisons, Principles of Internal Medicine (McGraw Hill, Inc., New York) for a description of standard treatments for peripheral neuropathies and/or for conditions that also present with symptoms of a peripheral neuropathy. The method for treating neuropathy may be a surgical method, a drug for treating neuropathy, a gene therapy method or a combination of the foregoing.

Surgical methods for treating a condition of vascular insufficiency include procedures such as bypass surgery, atherectomy, laser procedures, ultrasonic procedures, and balloon angioplasty to enhance vascularization of an ischemic tissue. In certain embodiments, the isolated angiogenic growth factor is administered to a subject in combination with a balloon angioplasty procedure. The isolated angiogenic growth factor is attached to the balloon angioplasty catheter in a manner which permits release of the isolated angiogenic growth factor at the site of the atherosclerotic plaque. The isolated angiogenic growth factor may be attached to the balloon angioplasty catheter in accordance with standard procedures known in the art. See, e.g., U.S. Pat. No. 5,652,225, entitled "Methods and products for nucleic acid delivery", issued to J. Isner, for a description of a balloon angioplasty procedure for delivering VEGF.

Additionally, the angiogenic growth factor may be administered in combination with the toxic agent which causes the neuropathy, e.g., a neoplastic agent, to alleviate the symptoms of peripheral neuropathy that are a side effect of the neoplastic agent.

The angiogenic growth factor also may be administered in combination with a drug for treating the condition which is believed to be associated with, or caused by, the peripheral neuropathy. For example, the angiogenic growth factor may be administered in combination with a drug for treating a diabetic condition (e.g., insulin), to alleviate the symptoms of peripheral neuropathy that are a side effect of the diabetic condition.

The above-described drug therapies are well known to those of ordinary skill in the art and are administered by modes known to those of skill in the art. The drug therapies are administered in amounts which are effective to achieve the physiological goals (to prevent or reduce the physiological consequences of a peripheral neuropathy), in combination with the isolated angiogenic growth factor(s) of the invention. Thus, it is contemplated that the drug therapies may be administered in amounts which are not capable of preventing or reducing the physiological consequences of the peripheral neuropathy when the drug therapies are administered alone but which are capable of preventing or reducing the physiological consequences of the peripheral neuropathy when administered in combination with the isolated angiogenic growth factors of the invention.

The isolated angiogenic growth factor may be administered alone or in combination with the above-described drug therapies as part of a pharmaceutical composition. Such a pharmaceutical composition may include the isolated angiogenic growth factor in combination with any standard physiologically and/or pharmaceutically acceptable carriers which are known in the art. The compositions should be sterile and contain a therapeutically effective amount of the isolated angiogenic growth factor in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the angiogenic growth factors, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Intramuscular administration is preferred; however other modes of administration may be acceptable including, e.g., other parenteral routes, oral, rectal, topical, nasal, or interdermal. The term "parenteral" includes subcutaneous, intravenous, intramuscular, or infusion.

The pharmaceutical compositions may conveniently be presented in unit dosage form and may be prepared by any of the methods well-known in the art of pharmacy. All methods include the step of bringing the angiogenic growth factors into association with a carrier which constitutes one or more accessory ingredients. In general, the compositions are prepared by uniformly and intimately bringing the angiogenic growth factors into association with a liquid carrier, a finely divided solid carrier, or both, and then, if necessary, shaping the product.

Other delivery systems can include time-release, delayed release or sustained release delivery systems such as those described in detail above. In general, such systems can avoid repeated administrations of the angiogenic growth factors, increasing convenience to the subject and the physician. Many types of release delivery systems are available and known to those of ordinary skill in the art. They include the above-described polymeric systems, as well as polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the angiogenic growth factor is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The isolated angiogenic growth factor may be administered alone or in combination with the above-described drug therapies by any conventional route, including injection or by gradual infusion over time. The administration may, for example, be intramuscular, intravenous, intraperitoneal, intra-cavity, subcutaneous, oral, or transdermal. When using the isolated angiogenic growth factor of the invention, direct administration to the nerve injury site, such as by administration in conjunction with a balloon angioplasty catheter or intramuscular injection, is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In general, the angiogenic growth factor nucleic acids can be administered to the subject (any mammalian recipient) using the same modes of administration that currently are used for gene therapy in humans (e.g., adenovirus-mediated gene therapy). Preferably, the angiogenic growth factor nucleic acid (contained in, or associated with, an appropriate vector) is administered to the mammalian recipient by balloon angioplasty catheter (described above), or intravascular, or, more preferably, intramuscular injection. A procedure for performing in vivo gene therapy for delivering a nucleic acid encoding an intact angiogenic growth factor (VEGF) to cells in vivo for treating a vascular injury is reported in U.S. Pat. No. 5,830,879, entitled "Treatment of vascular injury using vascular endothelial growth factor", issued to J. Isner.

As an illustrative example, a vector containing a VEGF nucleic acid is delivered to a site of vascular injury in a subject who is a candidate for such gene therapy. Then, the vector genetically modifies the target cells (e.g., endothelial cells, muscle cells, nerve cells) in vivo with DNA (RNA) encoding the VEGF. Such genetically modified cells express VEGF which is believed to directly or indirectly alleviate the symptoms of a peripheral neuropathy in vivo. Although not wishing to be bound to a particular theory or mechanism, it is believed that such genetically modified cells exhibit enhanced nerve regeneration in vitro and in vivo.

The invention will be more fully understood by reference to the following examples. These examples, however, are merely intended to illustrate the embodiments of the invention and are not to be construed to limit the scope of the invention.

EXAMPLES

Introduction:

The Examples employ certain procedures which are known in the art and which may have been published in issued U.S. patents or foreign patent documents, including the following documents:

| Patent/Serial/Publication No. | Title | Inventor |
|---|---|---|
| U.S. Pat. No. 5,830,879 | Treatment of vascular injury using vascular endothelial growth factor | J. Isner |
| U.S. Pat. No. 5,652,225 | Methods and products for nucleic acid delivery | J. Isner |
| U.S. Ser. No. 08/545,998 | Method for Treating Ischemic Tissue | J. Isner |
| U.S. Pat. No. 5,648,335; U.S. Pat. No. 5,633,228; and U.S. Pat. No. 5,569,648 | Prevention and treatment of peripheral neuropathy | M. Lewis, et al. |

Selected methods that previously have been described in the above-identified patent documents and that can be used in accordance with the methods of the instant invention are briefly summarized herein.

Method: Plasmids

Complementary DNA clones for recombinant human VEFG$_{165}$ isolated from cDNA libraries prepared from HL60 leukemia cells, were assembled into a simple eukaryotic expression plasmid that utilizes 736 bp cytomegalovirus promoter/enhancer to drive VEGF expression. Downstream from the VEGF cDNA is an SV40 polyadenylation sequence. Also included in this plasmid is a fragment containing the SV40 origin of replication that includes the 72 bp repeat, but this sequence is not functionally relevant (for autonomous replication) in the absence of SV40 T antigen. These fragments occur in the pUC118 vector which includes an *E. Coli* origin of replication and the β-galactosidase gene for ampicillin resistance. The biological activity of VEGF$_{165}$ secreted from cells transfected with this construct (phVEGF$_{165}$) was previously confirmed by evidence that media conditioned by transfected human 293 cells promoted the proliferation of capillary cells (Leung, et al, *Science*, 246:1306–9 (1989)).

The plasmid pGSVLacZ (courtesy of Dr. Claire Bonnerot) containing a nuclear targeted β-galactosidase sequence coupled to the simian virus 40 early promoters (Bonnerot, et al., *Proc Natl Acad Sci, U.S.A.*, 84:6795–9 (1987)) was used for all the control transfections.

Method: Animal Model

New Zealand white rabbits with operatively induced unilateral hindlimb vascular insufficiency, (Takeshita, et al., *Circulation*, 90:228–234 (1994); Takeshita, et al., *J. Clin. Invest.* 93:662–70 (1994); Pu, et al., *Circulation*, 88:208–215 (1993), were used to model both acute and chronic ischemia. All protocols were approved by the Institutional Animal Care and Use Committee. The care of animals complied with the guidelines of the Canadian Council of Animal Care, the Principles of Laboratory Animal Care, and the Guide for the Care and Use of Laboratory Animals (NIH publication No. 80-23, revised 1985). Fifty-nine male New Zealand White rabbits (mean weight=3 kg) were anesthetized with ketamine (50 mg/kg) and xylazine (5 mg/kg). Through a longitudinal incision performed in a medial thigh, the femoral artery was dissected free along its entire length, as were all major branches of the femoral artery, including the inferior epigastric, deep femoral, lateral circumflex and superficial epigastric arteries. After further dissecting the popliteal and saphenous arteries distally, the external iliac artery as well as all of the above arteries were ligated. Finally, the femoral artery was completely excised from its proximal origin as a branch of the external iliac artery to the point distally where it bifurcates into the saphenous and popliteal arteries.

Method: Intramuscular (IM) Gene Transfer

Acute Limb Ischemia. Twenty-eight rabbits were used to study the impact of IM gene transfer on acute hindlimb ischemia. Immediately following femoral artery excision as outlined above, five different sites in three major thigh muscles were injected directly with plasmid DNA using a 3 ml syringe and 27-gauge needle advanced through a small skin incision. For each injection, the tip of the needle was inserted into the adductor (2 sites), medial large (2 sites), and semimembranous muscles; care was taken, by directly visualizing each muscle during the injection, to avoid penetrating the muscle with the injectate. To the same end, the rate of injection was in each case slowed to approximately 5 seconds so that injected solution would not leak through the epimysium. This injection technique was used to administer a total volume of 2.5 ml of a) a 500 µg ph VEGF$_{165}$ in saline (n+8; b) 500 µg phVEGF$_{165}$ in 0.75% bupivacaine, previously shown to enhance transgene uptake by striated muscle (n+10) (Danko I, Gene Therapy, 1:114–21 (1994); or c) 500 µg pGSVLacZ encoding nuclear targeted β-galactosidase (n+10). After completing 5 injections (0.5 ml @ for each animal), the skin was then closed using 4.0 nylon.

Chronic Limb Ischemia. Thirty-one rabbits were used to study the effects of IM gene therapy for chronic hindlimb ischemia. The sole distinction between the chronic ischemia model and model of acute limb ischemia described above, is that an interval of 10 days was permitted for post-operative recovery, including development of endogenous collateral vessels. Accordingly, 10 days following femoral artery excision, the rabbits were returned to the catheterization laboratory. After completing baseline physiological measurements described below, IM gene transfer using the identical technique described above was performed with a) 500 μg phVEGF$_{165}$ diluted in 2.5 ml of saline (n=8); b) 500 μg phVEGF$_{165}$ diluted in 0.75% bupivacaine (n=8); c) 500 μg of pGSVLacZ diluted in 2.5 ml of saline; or d) 500 μg of pGSVLacZ diluted in 2.5 ml of 0.75% bupivacaine (n=8). In each case, after completing all 5 injections, the skin was closed as above.

VEGF Gene Expression in Skeletal Muscle. To evaluate expression of ph VEGF$_{165}$ gene in skeletal muscle, sixteen additional male New Zealand white rabbits from both acute and chronic ischemia models (2 rabbits at each time point) were sacrificed at 3, 7, 14, and 30 days post-transfection. The presence of human VEGF mRNA was detected using reverse transcription-polymerase chain reaction (RT-PCR) as previously described (Takeshita, et al., *Proc Natl Acad Sci*). To ensure specificity and avoid amplification of endogenous rabbit VEGF, primers were selected from a region which is not conserved among different species. Sequences of primers used were: 5'-GAGGGCAGAATCATCAC-GAAGT-3' (sense) (SEQ ID NO:1): 5'-TCCTATGTGCTG-GCCTTGGTGA-3' (antisense) (SEQ ID NO:2). RT-PCR products were analyzed by 2% agarose gel electrophoresis. DNA bands were visualized under UV illumination after staining with ethidium bromide.

Example 1

Define Certain Morphologic, Temporal, and Functional Aspects of Therapeutic Angiogenesis A. Cellular proliferation contributing to the development of the nascent collateral circulation is augmented in ischemic limbs in response to therapeutic angiogenesis.

We determined the extent to which proliferative activity of vascular cells is augmented during therapeutic angiogenesis with VEGF (Takeshita S, et al., *Am J Pathol* 1995;147: 1649–1660). Ten days following induction of limb ischemia by surgically excising femoral artery of rabbits, either VEGF (500–1,000 mg) or saline was administered as a bolus into the iliac artery of the ischemic limb. Cellular proliferation was evaluated by bromodeoxyuridine (BrDU) labeling for 24 hrs at day 0 (immediately prior to VEGF administration) and at days 3, 5, and 7 post-VEGF. EC proliferation in the midzone collaterals of VEGF-treated animals increased 2.8-fold at day 5 (p<0.05, vs. control), and returned to baseline levels by day 7. Smooth muscle cell proliferation in midzone collaterals also increased 2.7-fold in response to VEGF (p<0.05). No significant increase in cellular proliferation was observed in either the stem or re-entry collaterals. Reduction of hemodynamic deficit in the ischemic limb measured by lower limb blood pressure was documented at day 7 post-VEGF (p<0.01, vs. control). These data thus support the concept that increased cellular proliferation contributes to the formation of collateral vessels following therapeutic angiogenesis with VEGF.

Subsequently, we have similarly documented the time-course of cellular proliferative activity in a mouse model of hindlimb ischemia (Couffinhal T., et al., *Am J Pathol* 1998; 152:1667–1679). The femoral artery of one hindlimb was ligated and excised. Laser Doppler perfusion imaging (LDPI) was employed to document the consequent reduction in hindlimb blood flow which typically persisted for up to seven days. Serial in vivo examinations by LDPI disclosed that hindlimb blood flow was progressively augmented over the course of 14 days, ultimately reaching a plateau between 21 and 28 days. Morphometric analysis of capillary density performed at the same timepoints selected for in vivo analysis of blood flow by LDPI confirmed that the histologic sequence of neovascularization corresponded temporally to blood flow recovery detected in vivo. EC proliferation was documented by immunostaining for BrdU injected 24 hrs prior to each of these timepoints, providing further evidence that angiogenesis constitutes the basis for improved collateral-dependent flow in this animal model. BrdU staining was performed in the ischemic versus normal hindlimbs. Proliferative activity peaked at 7 days (1235±254 vs 8±14 BrdU-positive cells/mm$^2$ for the ischemic vs normal limbs respectively (p<0.001); proliferative activity was then subsequently reduced at days 14 and 21. Double immuno-labeling for BrdU and CD-31 demonstrated proliferating ECs in the ischemic limb. Most proliferating ECs localized to small capillaries, although EC proliferation was observed in small arteries as well. Capillary density and proliferative activity were also examined in mice treated with PF-4 and sacrificed 14 days after surgery. A significant decrease in capillary density (268±195 vs 1053±371 capillaries/mm$^2$, p<0.01) and EC proliferation (16±29 vs 935±239 BrdU-positive cells/mm$^2$, p<0.01) were found in PF-4 vs PBS-injected mice respectively.

Finally, in two patients who underwent amputations following VEGF gene therapy, EC proliferative activity in the ischemic limb has been documented as well, using double immunostaining for PCNA and CD31 (Baumgartner I, et al., *Circulation* 1998;97:1114–1123) (Isner J M, et al., *Lancet* 1996;348:370–374).

B. Therapeutic angiogenesis may be employed successfully to supplement established, native collateral circulation.

Long-term experiments regarding this issue are still ongoing. In the interim, however, we have documented by angiographic analysis supplemental collateral vascular development in patients with collateral vessels that had developed endogenously prior to gene transfer (Baumgartner I, et al., *Circulation* 1998;97:1114–1123) (Isner J M, et al., *J Vasc Surg* 1998;28:964–975). Thus the extent of collateral development appears to be influenced less by the extent of pre-existing collaterals than by other possible determinants.

C. Therapeutic angiogenesis preserves receptor-mediated endothelium-dependent flow in the rabbit ischemic hindlimb.

Disturbed endothelium-dependent blood flow has been previously shown to be a feature of native collateral vessels. We therefore investigated the hypothesis that administration VEGF may promote recovery of disturbed endothelium-dependent blood flow in our rabbit model of hindlimb ischemia (Bauters C, et al., *Circulation* 1995;91:2802–2809).

Ischemia was induced by ligation of external iliac artery and excision of femoral artery in one limb of NZW rabbits (day 0). Flow velocity was measured using a Doppler guidewire at rest and following serotonin and acetylcholine. Blood flow (ml/min) was calculated assuming a circular lumen geometry. In untreated control animals with an ischemic limb, serotonin administered at days 10 or 40 produced a decrease in hindlimb blood flow (71±2% and 33±6% reduction from baseline, respectively); in contrast, among animals treated with a single bolus dose of VEGF administered selectively into the internal iliac artery at day 10 and studied at day 40, serotonin produced an increase in flow (119±8% from baseline; p<0.05 vs controls). Acetylcholine induced only a moderate increase in flow in control animals (152±15% at day 10, 177±14% at day 40), in contrast to a profound increase among VEGF-treated animals studied at day 40 (254±25%; p<0.05 vs controls).

To our knowledge, these findings constitute the first demonstration of successful pharmacologic modulation of disturbed endothelium-dependent flow in the arterial circulation subserved by collateral vessels. This physiologic benefit complements previously reported anatomic findings suggesting a favorable impact of angiogenic growth factors on collateral-dependent limb ischemia.

Example 2

Investigation of Certain Conditional Factors which May Modulate the Outcome of Therapeutic Angiogenesis A. Hypoxia modulates the response to angiogenesis induced by VEGF and bFGF.

To evaluate this hypothesis, we investigated whether low oxygen tension or cytokines known to promote neovascularization in vivo could modulate the expression of VEGF or bFGF in human vascular smooth muscle cells (SMCs) (Brogi E, et al., Circulation 1994;90:649–652). SMCs were treated with platelet derived growth factor BB (PDGF BB) or transforming growth factor β1 (TGF-β1) or exposed to low oxygen tension in serum-free medium. Northern analysis detected low basal levels of VEGF and bFGF mRNA in extracts of unstimulated SMCs. However, both VEGF and bFGF transcripts increased following administration of PDGF BB (10 or 20 ng/ml) or TGF-β1 (0.1 or 1 ng/ml). Hypoxia was a potent stimulus for VEGF gene expression, but had no apparent effect on bFGF steady state mRNA levels. These results documented that certain indirect angiogenic cytokines, such as PDGF BB or TGF-β1, may act via induction of bFGF and VEGF gene expression in cells resident near ECs in vivo. Hypoxia constitutes a potent stimulus for VEGF gene expression, but does not regulate bFGF under the same experimental conditions.

We further investigated whether the role of human ECs might, under selected conditions, extend beyond that of a target to involve contingency synthesis of VEGF (Namiki A, et al., J Biol Chem 1995;270:31189–31195). In both unstimulated human umbilical vein ECs (HUVECs) or human derma-derived microvascular ECs (HMECs), Northern analysis detected no VEGF transcripts. Phorbol-12-myristate 13-acetate (PMA, $10^{-7}$ M) treatment, however, induced VEGF mRNA expression in both HUVECs and HMECs, peaking at 3 hrs and 6 hrs respectively, and returning to undetectable levels by 12 hrs. In vitro exposure of HUVECs to an hypoxic environment ($pO_2$=35 mmHg) for 12, 24 and 48 hrs, and HMECs for 6, 12, 24 and 48 hrs induced VEGF mRNA in a time-dependent fashion. Re-exposure to normoxia ($pO_2$=150 mmHg) for 24 hrs after 24 hrs of hypoxia returned VEGF mRNA transcripts to undetectable levels in HUVECs. Cobalt chloride ($Co^{2+}$) and nickel chloride ($Ni^{2+}$) treatment each induced VEGF mRNA in ECs. Cycloheximide treatment further augmented expression of VEGF mRNA induced by $Co^{2+}$, $Ni^{2+}$ and hypoxia in HUVECs. VEGF protein production in hypoxic HUVECs was demonstrated immunohistochemically. Conditioned media from hypoxic HUVECs caused a two-fold increase in the incorporation of tritiated thymidine. Finally, immune precipitates of anti-KDR probed with anti-P-tyr antibodies demonstrated evidence of receptor autophosphorylation in hypoxic, but not normoxic, HUVECs. These findings thus established the potential for an autocrine pathway that may augment and/or amplify the paracrine effects of VEGF in stimulating angiogenesis.

To determine if ECs expressed VEGF in vivo, in situ hybridization was performed using a murine $VEGF_{165}$ cRNA probe to identify VEGF mRNA in the mouse ischemic hindlimb (Couffinhal T., et al., Am J Pathol 1998; 152:1667–1679). Prior to surgery, scarce hybridization was detected in the ischemic limb. VEGF mRNA was also detected in ECs located in small capillaries or venules. In some cases, ECs of larger caliber veins also displayed positive hybridization for VEGF; VEGF expression among ECs of similar caliber arteries, however, was less frequent.

Finally, we investigated the impact of hypoxia or hypoxia-dependent conditions on VEGF receptor expression (Brogi E, et al., J Clin Invest 1996;97:469–476). HUVECs and microvascular ECs (MVECs) were exposed to direct hypoxia or to medium conditioned (CM) by myoblasts maintained in hypoxia for 4 days. Control ECs were maintained in normoxia or normoxia-CM. Binding of $^{125}$I-VEGF to ECs was then evaluated. Hypoxic treatment of ECs had no effect on $^{125}$I-VEGF binding. However, treatment of ECs with hypoxia-CM produced a 3-fold increase in $^{125}$I-VEGF binding, with peak at 24 h (p<0.001, ANOVA). Scatchard analysis disclosed that increased binding was due to a 13-fold increase in KDR receptors/cell, with no change in KDR affinity (Kd=260±51 pM, normoxia-CM versus Kd=281±94 pM, hypoxia-CM) and no change in EC number (35.6±5.9×$10^3$ ECs/cm$^2$, normoxia-CM versus 33.5±5.5×$10^3$ ECs/cm$^2$, hypoxia-CM). Similar results were obtained using CM from hypoxic SMCs. KDR upregulation was not prevented by addition to the hypoxia-CM of neutralizing antibodies against VEGF, tumor necrosis factor-a, transforming growth factor-b1 or bFGF. Similarly, addition of VEGF or lactic acid to the normoxia-CM had no effect on VEGF binding. These experiments implicated a paracrine mechanism initiated by hypoxia that induces KDR receptor upregulation in ECs. Hypoxic cells, not only can produce VEGF, but can also modulate its effects via paracrine induction of VEGF receptors in ECs.

B. Hypercholesterolemia attenuates the response to therapeutic angiogenesis.

We investigated the anatomic extent and functional capacity of the collateral bed which develops in response to limb ischemia in a well characterized animal model of spontaneous hypercholesterolemia, the Watanabe heritable hyperlipidemic (WHHL) rabbit (Van Belle E, et al., Circulation 1997;96:2667–2674). We further characterized the impact of exogenous angiogenic cytokine administration on collateral vessel development and function in the same animal model. Weight-matched 6-month old male homozygous WHHL (n=9) and normal NZW (n=9) rabbits underwent operative resection of one femoral artery. Ten days later, the ischemic hindlimb was evaluated for collateral vessel formation, blood flow, and tissue damage. Collateral vasculature was less extensive among WHHL than NZW, as indicated by a significant reduction in angiographic score (0.19±0.02 vs 0.35±0.03; P<0.001) and capillary density (46.4±4.1 vs 78.9±4.6/mm$^2$, P<0.0002). This was associated with a reduction in calf blood pressure index (9.5±3.5 vs 32.8±2.8%, P<0.0001), arterial blood flow (7.5±0.6 vs 13.6±0.7 mL/min, P<0.0001), muscle perfusion index (40.1±3.2 vs 65.9±2.0%, P<0.0001), and an increase in muscle necrosis (48.16±5.41 vs 25.90±3.83% negative 2,3, 5-triphenyltetrazolium chloride staining, P<0.004). Treatment of WHHL rabbits (n=9) with recombininant human VEGF produced a statistically significant improvement in all functional as well as anatomic indices of collateral development. Thus, collateral vessel development associated with hindlimb ischemia in vivo is severely attenuated in an animal model of spontaneous hypercholesterolemia, but may be nevertheless augmented by administration of angiogenic cytokines.

These findings were confirmed in a murine model of hypercholesterolemia (Couffinhal T, et al., *Circulation* 1999; (In Press)), the ApoE$^{-/-}$ mouse, with unilateral hindlimb ischemia. Hindlimb blood flow and capillary density were markedly reduced in ApoE$^{-/-}$ mice vs C57 controls. This was associated with reduced expression of VEGF in the ischemic limbs of ApoE$^{-/-}$ mice. Cell-specific immunostaining localized VEGF protein expression to skeletal myocytes and infiltrating T cells in the ischemic limbs of C57 mice; in contrast, T cell infiltrates in ischemic limbs of ApoE$^{-/-}$ mice were severely reduced (despite normal absolute T cell counts in these animals). The critical contribution of T cells to VEGF expression and collateral vessel growth was reinforced by the finding of accelerated limb necrosis in athymic nude mice with operatively induced hindlimb ischemia. Adenoviral VEGF gene transfer to ApoE$^{-/-}$ mice resulted in marked augmentation of hindlimb blood flow and capillary density. These findings thus underscore the extent to which hyperlipidemia adversely affects native collateral development, but does not preclude augmented collateral vessel growth in response to exogenous cytokines. Moreover, results obtained in the ApoE$^{-/-}$ and athymic nude mice imply a critical role for infiltrating T cells as a source of VEGF in neovascularization of ischemic tissues.

C. The response to therapeutic angiogenesis is attenuated in a diabetic animal model of hindlimb ischemia.

We determined if diabetes could: 1) impair the development of new collateral vessel formation in response to tissue ischemia, and 2) inhibit cytokine-induced therapeutic neovascularization (Rivard A, et al., *Am J Pathol* 1999; 154:355–364). Hindlimb ischemia was created by femoral artery ligation in non-obese diabetic mice (NOD mice, n=20) and in control C57 mice (n=20). Hindlimb perfusion was evaluated by serial laser Doppler studies after surgery. In NOD mice, measurement of the Doppler flow ratio (DFR) between the ischemic and the normal limb indicated that restoration of perfusion in the ischemic hindlimb was significantly impaired. At day 14 after surgery, DFR in the NOD mice was 0.49±0.04 vs. 0.73±0.06 for the C57 mice ($p \leq 0.005$). This impairment in blood flow recovery persisted throughout the duration of the study, with DFR values at day 35 of 0.50±0.05 vs 0.90±0.07 in the NOD and C57 mice respectively ($p \leq 0.001$). CD31 immunostaining confirmed the laser Doppler data by showing a significant reduction in capillary density in the NOD mice at 35 days after surgery (302±4 capillaries/mm$^2$ vs 782±78 in C57 mice ($p \leq 0.005$). The reduction in neovascularization in the NOD mice was the result of a lower level of VEGF in the ischemic tissues, as assessed by Northern blot, Western blot and immunohistochemistry. The central role of VEGF was confirmed by showing that normal levels of neovascularization (compared to C57) could be achieved in NOD mice that had been supplemented for this growth factor via IM injection of an adenoviral vector encoding for VEGF. We concluded that: 1) diabetes impairs endogenous neovascularization of ischemic tissues; 2) the impairment in new blood vessel formation results from reduced expression of VEGF; and 3) cytokine supplementation achieved by IM adeno-VEGF gene transfer restores neovascularization in a mouse model of diabetes.

Example 3

The Impact of Growth Factor Selection, Mode of Delivery, and Use of Adjunctive Therapies in Optimizing the Anatomic and Physiologic Outcomes of Therapeutic Angiogenesis A. The character and magnitude of cellular proliferation observed in response to VEGF may be modified by co-administration of a second angiogenic growth factor.

To test this hypothesis, we evaluated the extent of neovascularization which was achieved in vivo following intra-arterial administration of VEGF (500 µg) alone, bFGF (10 µg) alone, and VEGF(500 µg)+bFGF(10 µg) all as recombinant protein, to the internal iliac artery of the rabbit ischemic hindlimb (Asahara T, et al., *Circulation* 1995;92: II-365-II-371). Augmentation of calf blood pressure ratio as well as papaverine-induced maximum flow reserve was significantly ($p<0.05$) greater in the VEGF+bFGF group than the VEGF, bFGF, or saline control groups. The extent of neointimal thickening in the internal iliac artery at day 30 was not significantly different among the four experimental groups. This study thus demonstrated that co-administration of VEGF and bFGF produces a greater (and parenthetically more rapid) improvement in vascularity than either VEGF or bFGF alone.

We have also demonstrated that the pleiotropic effects of certain growth factors may potentiate angiogenesis due to a combination of direct effects on EC proliferation and migration, and indirect effects that result in the generation of other potent EC mitogens from non-EC populations (Van Belle E, et al., *Circulation* 1998;97:381–390). In the case of hepatocyte growth factor (HGF), the synergistic effect, which results from simultaneous administration of VEGF in vitro, is reproduced in vivo by HGF-induced upregulation of VEGF in vascular SMCs. HGF is a pleiotropic growth factor, which stimulates proliferation and migration of ECs via the c-Met receptor, present on ECs as well as other cell types, including SMCs. We studied the effects of recombinant human (rh) HGF in vitro, and in vivo in our rabbit model of hindlimb ischemia. We further compared these effects with those of recombinant human VEGF (rh-VEGF$_{165}$).

In vitro, rhHGF and rhVEGF$_{165}$ exhibited similar effects on proliferation and migration of ECs. When both cytokines were administered together, the result was an additive effect on EC proliferation, and a synergistic effect on EC migration. Application of rhHGF to cultures of human SMCs resulted in the induction of VEGF mRNA and protein. In vivo, administration of rhHGF (500 µg×3) was associated with significant improvements in collateral formation ($p<0.001$) and regional blood flow ($p<0.0005$), and with a significant reduction in muscle atrophy ($p<0.0001$). These effects were significantly more pronounced than those of rhVEGF$_{165}$ administered according to the same protocol ($p<0.05$). Neither remote angiogenesis nor other pathologic sequellae were observed with either rhHGF or rhVEGF$_{165}$. Thus, the finding of a potentiated angiogenic effect of rhHGF via induction of VEGF constitutes what is in essence paracrine amplification of angiogenesis Finally, we tested the hypothesis that gene transfer of plasmid DNA encoding angiopoietin1 (Ang1) and Ang2 could modulate collateral vessel development in a rabbit model of hindlimb ischemia (Shyu K-G, et al., *Circulation* 1998;98:2081–2087). Ang1, but not Ang2, gene transfer produced anatomic and physiologic evidence of enhanced collateral vessel formation because Ang1 is known not to have any effect on EC proliferation, it is possible that a synergistic effect between exogenous Ang1 and endogenous VEGF expression accounts for the finding of enhanced collateral development in response to Ang1.

B. The magnitude of angiogenesis developing in response to administration of exogenous growth factors may be augmented by administration of heparin.

Ten days after excision of the femoral artery in one limb of NZW rabbits, heparin (800 IU, n=13), VEGF (1 mg, n=3; 5 mg, n=5), heparin (800 IU)+VEGF (1 mg, n=5; 5 mg, n=7), or saline (n=8) was injected as a single bolus in a marginal ear vein (Bauters C et al., *J Vasc Surg* 1995;21: 314–325). Collateral vessel formation and limb perfusion were assessed 10 and 30 days after treatment. Animals in both VEGF-treated groups had a significantly higher (p<0.01) increase in calf blood pressure ratio at day 10 (control=0.44±0.02; heparin=0.47±0.02; VEGF=0.60±0.01; [heparin+VEGF]=0.61±0.02) and day 30 (control=0.49±0.05; heparin=0.48±0.02; VEGF=0.70±0.03; [heparin+VEGF]=0.73±0.03). Both VEGF-treated groups had a significantly higher (p<0.05) angiographic score at day 30 (control=0.28±0.01; heparin=0.28±0.01; VEGF=0.37±0.01; [heparin+VEGF]=0.38±0.02). Maximum flow reserve at day 30 in the ischemic limb was higher (p<0.05) in VEGF-treated rabbits (control=1.87±0.07; heparin=1.92±0.08; VEGF=2.42±0.16; [heparin+VEGF]=2.33±0.12). Capillary density was higher (p<0.01) in the ischemic muscles of VEGF-treated rabbits (control=156±10/mm$^2$; heparin=178±8/mm$^2$; VEGF=230±10/mm$^2$; [heparin+VEGF]=233±8/mm$^2$). This series of in vivo experiments demonstrated that intravenous administration of VEGF, with or without heparin, results in both anatomic and physiologic evidence of enhanced collateral vessel formation in the rabbit ischemic hindlimb.

C. Coincident activation of plasminogen facilitates therapeutic angiogenesis.

The requirement that ECs must remove certain constraining physical influences, including the attachment to their underlying basement membrane and the more peripheral barrier posed by their extracellular matrix, to facilitate cell movement for development of a neovascular sprout, represents for angiogenesis a fundamental tenet (Vernon R B, et al., *Am J Pathol* 1995;147:873–883). Houck et al (Houck K A, et al., *J Biol Chem* 1992;267:26031–26037) previously reported that cleavage by plasmin of VEGF$_{189}$ at its —COOH terminus generates a 34 kD proteolytic fragment (cl-VEGF$_{189}$) which is mitogenic for ECs and active as a permeability agent. Park et al (Park J E, et al., *Mol Biol Cell* 1993;4:1317–1326) have reported that longer forms of VEGF are stably incorporated into the extracellular matrix, but can become available in diffusible form when the matrix is degraded by plasmin. We are currently investigating the possibility that coordinated extracellular matrix degradation—achieved by generating plasmin via administration of recombinant t-PA or co-transfection of plasmid cDNA encoding t-PA—may facilitate therapeutic angiogenesis.

D. The magnitude of the angiogenic response does not vary as a function of the distance from the ischemic site at which VEGF is administered.

The series of in vivo experiments described above (Example 3,B) established that intravenous administration of VEGF, with or without heparin, results in both anatomic and physiologic evidence of enhanced collateral vessel formation in the rabbit ischemic hindlimb (Bauters C, et al., *J Vasc Surg* 1995;21:314–325). A similar series of experiments demonstrated that IM administration of VEGF recombinant protein improved hindlimb perfusion to a similar extent as was seen with intra-arterial (and intravenous) delivery of the protein (Takeshita S, et al., *Circulation* 1994;90:II-228-II-234).

E. The magnitude of angiogenesis observed in response to VEGF varies as a function of the isoform of VEGF employed.

Plasmid DNA encoding each of the three principal human VEGF 1 (VEGFA) isoforms (phVEGF$_{121}$, phVEGF$_{165}$, or phVEGF$_{189}$) was applied to the hydrogel polymer coating of an angioplasty balloon, and delivered percutaneously to one iliac artery of rabbits with operatively induced hindlimb ischemia (Takeshita S, et al., *Lab Invest* 1996;75:487–502). Compared to control animals transfected with LacZ, site-specific transfection of phVEGF resulted in augmented collateral vessel development documented by serial angiography, improvement in calf blood pressure ratio (ischemic/normal limb), resting and maximum blood flow, and capillary/myocyte ratio. Similar results were obtained with phVEGF$_{121}$, phVEGF$_{165}$, and phVEGF$_{189}$, suggesting that these isoforms are biologically equivalent with respect to in vivo angiogenesis. The fact that viral or other adjunctive vectors were not required further suggests that secreted gene products may have potential therapeutic utility even when the number of successfully transfected cells remains low. Arterial gene transfer of naked DNA encoding for a secreted angiogenic cytokine thus represents a potential alternative to recombinant protein administration for stimulating collateral vessel development.

F. Therapeutic angiogenesis may be effectively performed using direct intramuscular (IM) administration of the gene encoding VEGF.

Striated muscle had been shown to be capable of taking up and expressing foreign genes transferred in the form of naked plasmid DNA, though typically with a low level of gene expression. We had shown, however, that in the case of genes which encode secreted proteins, low transfection efficiency did not preclude bioactivity of the secreted gene product (Takeshita S, et al., *Lab Invest* 1994;71:387–391) (Losordo D W, et al., *Circulation* 1994;89:785–792). Accordingly, we investigated the hypothesis that IM gene therapy with naked plasmid DNA encoding VEGF could augment collateral development and tissue perfusion in the rabbit ischemic hindlimb (Tsurumi Y, et al., *Circulation* 1996;94:3281–3290).

Ten days after ischemia was induced in one rabbit hindlimb, 500 µg of phVEGF$_{165}$, or the reporter gene LacZ, were injected IM into the ischemic hindlimb muscles. Thirty days later, angiographically recognizable collateral vessels and histologically identifiable capillaries were increased in VEGF-transfectants compared to controls. This augmented vascularity improved perfusion to the ischemic limb, documented by a superior calf blood pressure ratio for phVEGF$_{165}$ (0.85±0.05) vs. controls (0.64±0.05, p<0.01); improved blood flow in the ischemic limb (measured using an intra-arterial Doppler wire) at rest (phVEGF$_{165}$=21.3±3.9, control=14.6±1.6 ml/min, p<0.01) and following a vasodilator (phVEGF$_{165}$=54.2±12.0, control=37.3±8.9, p<0.01); and increased microspheres in the adductor (phVEGF$_{165}$=4.3±1.6, control=2.9±1.2 ml/min/100 g tissue, p<0.05), and gastrocnemius (phVEGF$_{165}$=3.9±1.0, control=2.8±1.4 ml/min/100 g tissue, p<0.05) muscles of the ischemic limb. These experiments established that ischemic skeletal muscle constituted a promising target for gene therapy with naked plasmid DNA. IM transfection of genes encoding angiogenic cytokines, particularly those which are naturally secreted by intact cells, thus appeared to represent an alternative treatment strategy for patients in whom extensive vascular disease prohibited access to the lower extremity vasculature otherwise required for intra-arterial catheter-based gene transfer.

Based on this animal data, we initiated a phase I clinical trial to (1) document the safety and feasibility of IM gene transfer using naked plasmid DNA encoding VEGF, and (2) analyze potential therapeutic benefits in patients with CLI (Baumgartner I, et al., *Circulation* 1998;97:1114–1123) (Isner J M, et al., *J Vasc Surg* 1998;28:964–975).

Gene transfer was performed in 10 limbs of 9 patients with non-healing ischemic ulcers (n=7/10) and/or rest pain (n=10/10) due to peripheral arterial disease. A total dose of 4000 μg of phVEGF$_{165}$ was injected directly into the muscles of the ischemic limb. Gene expression was documented by a transient increase in serum levels of VEGF monitored by ELISA assay. The ankle-brachial index improved significantly (0.33±0.05 to 0.48±0.03, p=0.02), new collateral blood vessels were directly visualized by contrast angiography in 7 limbs, and magnetic resonance angiography showed qualitative evidence of improved distal flow in 8 limbs. Ischemic ulcers healed or markedly improved in 4/7 limbs, including successful limb salvage in 3 patients recommended for below-knee amputation. Tissue specimens obtained from an amputee 10 wks after gene therapy showed foci of proliferating ECs by immunohistochemistry. PCR and Southern blot analyses indicated persistence of small amounts of plasmid DNA. Complications were limited to transient lower extremity edema in 6 patients, consistent with VEGF-enhancement of vascular permeability.

These findings thus demonstrated that IM injection of naked plasmid DNA may achieve constitutive overexpression of VEGF sufficient to induce therapeutic angiogenesis in selected patients with CLI.

Most recently, we adapted the use of IM phVEGF$_{165}$ gene transfer to investigate gene therapy for therapeutic angiogenesis in patients with myocardial ischemia (Losordo DW, et al., *Circulation* 1998;98:2800–2804). A phase 1 clinical study was initiated to determine the safety and bioactivity of direct intramyocardial gene transfer of VEGF as sole therapy for patients with symptomatic myocardial ischemia.

VEGF gene transfer (GTx) was performed in 5 patients (all male, ages 53–71) with angina due to angiographically documented coronary artery disease (CAD) who had failed conventional therapy (drugs, angioplasty surgery). Naked plasmid DNA encoding VEGF (phVEGF$_{165}$) was injected directly into the ischemic myocardium via a "mini" left anterior thoracotomy. Injections caused no changes in heart rate (pre-GTx=75±15/min vs post-GTx=80±16/min, p=NS), systolic BP (114±7 mmHg vs 118±7 mm Hg, p=NS), or diastolic BP (57±2 mmHg vs 59±2 mmHg, p=NS). Ventricular arrhythmias were limited to single unifocal premature beats at the moment of injection. Serial ECGs showed no evidence of new myocardial infarction in any pt. Intra-operative blood loss was 0–50 cc and total chest tube drainage was 110–395 cc. Cardiac output fell transiently post-op but increased within 24 hrs (pre-anesthesia=4.8±0.4 vs post-anesthesia=4.1±0.3 vs 24 hrs post-operatively=6.3±0.8, p=0.02). Time to extubation following closure was 18.4±1.4 min and avg post-op hospital stay was 3.8 days. All patients had significant reduction in angina (NTG use=53.9±10.0/wk pre-GTx vs 9.8±6.9/wk post-GTx, p<0.03). Post-operative left ventricular ejection fraction (LVEF) was either unchanged (n=3) or improved (n=2, mean increase in LVEF=5%). Objective evidence of reduced ischemia was documented using dobutamine SPECT-sestamibi imaging in all patients. Coronary angiography showed improved Rentrop score in 5/5 patients.

This initial experience with naked gene transfer as sole therapy for myocardial ischemia suggested that direct intramyocardial injection of naked plasmid DNA via a minimally invasive chest wall incision is safe and may lead to reduced symptoms and improved myocardial perfusion in selected patients with chronic myocardial ischemia. As of February, 1999, a total of 23 patients have been treated in this fashion with similar results (Symes J F, et al., *Ann Thorac Surg* 1999).

In summary, the above-described experiments extended the notion of therapeutic angiogenesis from in vitro studies and animal models to patients with lower extremity and myocardial ischemia.

Example 4

Peripheral Neuropathy

1. Neurological findings in patients undergoing phVEGF$_{165}$ gene transfer.

Methods and results: We prospectively evaluated neurological and neurophysiological findings in patients undergoing phVEGF$_{165}$ gene transfer for critical limb ischemia (CLI). All patients were evaluated by two neurologists, one performing clinical assessment, and one performing electrophysiologic testing. Both were blinded to each other's results, and both were blinded to the results of patients' vascular examinations. Furthermore, at follow-up examinations, both were blinded to results of previous examinations. Quantitative sensory testing was performed using CASE IV (Computer Aided Sensory Evaluator, a quantitative sensory testing device for thermal pain and vibration thresholds (Dyck P J, et al., *Diabetes Care* 1987;10:432–440)). Tibial motor, peroneal motor, and sural sensory electrophysiologic studies were performed using standard techniques. Both lower extremities were studied, except in patients in whom the contralateral, non-treated limb was not available due to previous amputation. A total of 24 limbs have thus far been analyzed before and 3 mo after gene transfer; 19 of these have been followed to 6 months.

These findings suggest that therapeutic angiogenesis have a favorable impact on established ischemic peripheral neuropathy. With regard to symptoms, for example, as early as 3 mo, Symptom Score, encompassing 5 neuropathy-related symptoms, decreased (i.e. improved) from (m±SEM) 3.3±0.5 to 1.7±0.4 (p<0.01). Sensory Disability Score decreased from 9.5±1.3 to 7.4±1.2 (p<0.01). By 6 mo, Symptom Score decreased to 1.1±0.4 (p<0.01 vs baseline of 3.4). Sensory Disability Score likewise decreased to 6.3±1.4 (p=0.01 vs baseline 9.5±1.3), along with a reduction in Total Disability Score (12.7±2.1 to 9.2±1.7, p=0.01). Vibration threshold decreased (i.e. improved) from 21.0±0.9 to 19.8±1.0, p=0.04. Moreover, by 6 months, improvement in objective indices of nerve function became manifest. Peroneal motor nerve amplitude increased from 2.1±0.6 to 2.8±0.6 (p=0.03). In no case did clinical examination or electrodiagnostic studies show statistically significant improvement for measurements recorded from the contralateral, non-treated lower extremity. The percent change in peroneal motor amplitude in the treated vs untreated leg for each of the 19 patients followed for 6 months (one patient, who began with an amplitude of 0 and increased to 0.2 is not shown); illustrates that increases were observed in three insulin-requiring diabetics (patients 1,5, and 11). Also included was one patient in whom we documented the appearance of a previously absent potential. For the group as a whole, the percent increase in peroneal amplitude (50.3±21.0) exceeded the change observed in the non-treated leg (−10.8±7.9) to a statistically significant degree (p=0.02). Similarly, the sum of motor amplitude increased 16.5±8.7% vs the non-treated leg (−8.8±6.5), (p=0.04).

Conclusions: This prospective study—the first to our knowledge to investigate the impact of therapeutic angiogenesis on peripheral nerve function in patients with limb ischemia—showed evidence of improvement in peripheral nerve function in patients undergoing phVEGF$_{165}$ gene transfer.

2. Adaptation of the rabbit ischemic hindlimb model for the investigation of ischemic peripheral neuropathy.

Methods and results: The rabbit model of hindlimb ischemia has been extensively characterized in our laboratory and frequently utilized to investigate strategies of therapeutic angiogenesis. We therefore undertook a series of preliminary experiments to determine the extent of peripheral neuropathy which might accompany the development of vascular insufficiency in this model.

Determination of normal electrophysiologic parameters. All protocols were approved by the Institutional Animal Care and Use Committee at St. Elizabeth's Medical Center. Male NZW rabbits 5–6 yrs of age (mean weight=5 kg) were used for all experiments. Pilot experiments performed in our laboratory showed that when hindlimb ischemia is created in young (6–8 mo) NZW rabbits, development of neuropathy is transient and of unpredictable magnitude. We therefore performed pilot experiments in old (5 yrs) rabbits, in which angiogenesis was shown to be retarded (Rivard A, et al., *Circulation* 1999;99:311–120) and documented persistent and profound neurophysiologic abnormalities. Before recordings from ischemic limbs could be made, it was necessary to document the electrophysiologic responses recorded from the rabbits' non-ischemic hindlimb. Motor and sensory nerve potentials were recorded from both limbs of 8 rabbits with intact femoral arteries. Data were considered as mean±standard error of the (m±SEM). Compound muscle action potentials (CMAPs) were 16.0±1.2 m V in the left limb and 16.4±0.9 mV in the right limb (p=ns). Sensory nerve action potentials (SNAPs) were 7.7±0.8 µV in the left limb vs 8.1±1.1 µV in the right limb (p=ns). (Neurophysiologic recordings in the non-ischemic limbs of old rabbits were not different from those recorded in non-ischemic limbs of young rabbits).

Induction of ischemia in the rabbit hindlimb. Unilateral hindlimb vascular insufficiency was operatively created in 10 rabbits using previously published techniques (Takeshita S, et al., *J Clin Invest* 1994;93:662–670).

Verification of ischemic peripheral neuropathy. After surgical induction of unilateral hindlimb ischemia, rabbits were allowed to recover for 5 days. Electrophysiologic recording of peripheral nerve function in the ischemic and non-ischemic limbs was then performed under general anesthesia on a weekly basis for 3 months CMAPs and SNAPs were recorded. Motor nerve conduction velocities (MCV) and sensory nerve conduction velocities (SCV) were calculated. Concomitantly, the calf blood pressure ratio, defined as the ratio of systolic pressure of the ischemic limb to that of the normal limb, was determined for each rabbit using standard techniques. At the defined end point, 12 wks after induction of ischemia, rabbits also underwent selective angiography of the internal iliac artery as previously described (Takeshita S, et al., *J Clin Invest* 1994;93:662–670).

The development of hindlimb ischemia had a profound effect on peripheral nerve function. Data were considered to represent function in right (ischemic) limb as a percentage of that recorded in left (non-ischemic) limb. Motor nerve amplitudes, indicated by CMAP, dropped to zero post-operatively before they became detectable again 4 wks later; at 8 wks post-operatively, CMAPs were still only 10 to 15% of normal. From wk 8 on, CMAPs increased in a nearly linear fashion, improving to 50–60% of normal by wk 10, with no further changes through wk 12 (56.2±7.3%). MCV behaved similarly: ischemic limbs displayed non-determinable conduction velocities up to wk 3. From wk 4 on, MCV increased in a nearly linear pattern, peaking at 87.4±3.6% of normal by wk 12.

In contrast to motor nerve parameters, SNAPs did not drop to zero level following induction of ischemia, but did remain depressed at 17–22% of normal between wks 1 to 4 following induction of ischemia. From then on, SNAPs increased to 51.7±5.1% of normal at wk 12. In contrast to MCV and CMAP, which were undetectable after the induction of ischemia, SCVs were initially reduced to approximately 20%, before they started to rise at wk 3 and by wk 12 were 98.9±0.1% of normal. Ischemia reduced calf blood pressure ratio to 22.9±5.4% at wk 1. An almost linear increase in calf blood pressure ratio peaked at 79.0±9.0% at wk 12. Finally, morphometric angiographic analysis, performed at wk 12, revealed that the angiographic score (quantitative analysis of vascular density based on contrast angiograms for ischemic limbs was 44.8±4.5% of non-ischemic limbs, consistent with endogenous neovascularization described previously for this model (Takeshita S, et al., *J Clin Invest* 1994;93:662–670). Pathologic findings included focal loss of axons and disrupted myelin sheaths.

Conclusion: These findings indicate that hindlimb ischemia causes a severe peripheral neuropathy which affects both motor and sensory nerve functions. The rabbit model of hindlimb ischemia thus represents a suitable tool for the investigation of ischemic peripheral neuropathy.

3. Therapeutic angiogenesis attenuates the development of ischemic peripheral neuropathy.

Methods and results. Previous work from our laboratory has demonstrated that IM ph VEGF$_{165}$ gene transfer performed at the time of surgery to create unilateral hindlimb ischemia results in accelerated revascularization of the ischemic hindlimb, in comparison to control animals injected with a reporter gene (Tsurumi Y, et al., *Circulation* 1996;94:3281–3290). Accordingly, we performed a pilot study involving 10 rabbits, each of which received 5 injections of phVEGF$_{165}$ (100 µg @) into the adductor (2 sites), medial large (2 sites), and semimembranosus (one site) muscles at the time the animals underwent unilateral excision of the femoral artery to create hindlimb ischemia. Following surgery and gene transfer, rabbits underwent electrophysiologic and vascular examinations on a weekly basis. Immediately prior to sacrifice at 12 wks, selective angiography was performed. Postmortem examination included analysis of capillary/myocyte ratios and morphometric examination of nerve tissue sections.

One week post-surgery, CMAPs recorded in the ischemic limb were reduced to 36.8±9.1% of that recorded from the left limb. At wk two, however, CMAPs had improved to 49.9±0.5% of normal, and by 3 wks improved further to 82.0±3.4% of normal. CMAP ratios for wks 8 to 12 displayed a plateau-like pattern with values ranging from 83.9±1.3% at wk 8 to 90.5±4.3% at wk 12. In comparison, CMAPs for the controls were 10.9±2.9% of normal at wk 8, and 56.2±7.3% at wk 12. From wk 8 to wk 12, CMAPs were significantly higher at each timepoint in day 0-treated rabbits.

Measurements of MCV demonstrated a moderate drop in conduction velocity for a brief period of two wks after the induction of ischemia (83.5±11.0% and 89.9±7.1% at wks 2 and 3, respectively). MCVs at these 2 timepoints were significantly different from values in the non-ischemic limb. Thereafter, however, MCV recovered to normal values, from wk 4 through wk 12.

Examination of sensory nerve function disclosed a reduction in SNAPs from 100% at baseline to 70.2±11.3% within the first wk after surgery. This parameter continued to be significantly lower than normal up to wk 4. Neurophysiological assessment at wk 5, however, disclosed improvement in SNAPs to 99.6±16.6%, hence no longer significantly different from normal baseline values. No further significant change in SNAPs was observed up to wk 12 when the animals were sacrificed.

SCVs were also recorded in this study group and were found to be only slightly depressed within the first wks after the onset of ischemia. The lowest SVC was 90.6±7.3% at wk 3. All other timepoints were even closer to normal or absolutely normal, and none of the values taken differed significantly from normal values.

At each timepoint employed for neurophysiological examinations, blood pressure ratios for the rabbits' hindlimbs were recorded as well. The results with the motor nerve parameters show that post-operatively there was an expected drop in the blood pressure ratio to 38.0±9.1% of normal. Three wks post-operatively, the calf blood pressure ratio had risen again to 82.9±4.7%. Further follow-up examinations showed a progressive rise in blood pressure ratio to 97.2±1.1% at wk 12 before sacrifice. Pathologic observations indicated improved preservation of axons and myelin sheaths, compared to untreated animals.

Conclusion: Day-0 IM gene transfer of phVEGF$_{165}$ prevented CMAPs as well as SNAPs from dropping to unrecordably low levels, and led to significantly faster recovery of CMAPs and SNAPs. An even more obvious impact of treatment was seen on MCV and SCV, both of which were only mildly reduced within the first 3 wks after ischemia. Improvement in calf blood pressure ratio paralleled these neurophysiologic findings.

4. Therapeutic angiogenesis promotes recovery of established ischemic peripheral neuropathy.

Methods and results: To investigate whether established ischemic neuropathy can be reversed by therapeutic angiogenesis, 10 rabbits underwent excision of the femoral artery followed by a 10 day interval to permit development of severe hindlimb ischemia and hence ischemic neuropathy. At day 10, rabbits underwent phVEGF$_{165}$ gene transfer for therapeutic angiogenesis as outlined above. Neuroelectrophysiologic and blood pressure measurements were again performed on a weekly basis according to the protocol described above.

Within the 10-day period between induction of ischemia and treatment, CMAPs dropped to undetectable levels. At week 4 (2.5 wks post-treatment), amplitudes were 16.8±1.6% of baseline. Subsequent follow-up examinations documented improvement in CMAPs, increasing to 44.1±4.7% at wk 6, and 69.1±2.2% at the endpoint (wk 12 after the induction of ischemia, i.e. 10.5 wks post-gene transfer).

MCVs were detectable neither at first examination after excision of the femoral artery, nor briefly after gene therapy. However, by wk 3 (1.5 wks after gene transfer), MCV increased to 35.0±14.1% of normal, and one wk later to 74.8±3.2% of normal. By wk 12, MCV in the ischemic limb was restored to 86.5±3.9% of normal.

SNAPs decreased to 38.3±15.2% of normal following induction of ischemia. The first significant change in SNAPs thereafter was detectable 2.5 wks after gene therapy (wk 4), when the SNAP ratio improved to 64.9±8.4%. By wk 6, SNAPs had reached normal values again (103.3±10.5%), and at wk 12 were 96.9±4.9%.

SCVs, in contrast to the MCVs, were less severely affected by induction of ischemia: no significant alteration (in comparison to the contralateral non-ischemic contralateral limb) could be detected.

Blood pressure measurements in this study group disclosed the anticipated reduction in limb perfusion post-surgery (blood pressure ratio in the ischemic to normal limb=21.8±5.4%). Following gene therapy, blood pressure ratio showed an almost linear increase, peaking at 95.2±0.3% by wk 12.

Conclusion: For SNAPs, the day 0-treated group showed the most favorable outcome in terms of minimally impaired nerve function and quick recovery. In the day 10-treated group, however, SNAPs were also restored earlier, reaching normal function again by 4.5 wks after gene therapy. SNAPS in untreated animals remain reduced (51.7±5.1% of normal values). CMAP recovery of day 0-treated animals was fastest and most complete, whereas onset of recovery in untreated rabbits was delayed to 6.5 wks after surgery. CMAPs in the day 10-treatment group recovered faster than those in untreated rabbits. These findings suggest a favorable effect of therapeutic angiogenesis on the development of ischemic peripheral neuropathy.

5. Expression of VEGF and VEGF receptor by Schwann cells in vitro

Methods and results: NZW rabbits were sacrificed under aseptic conditions using an intracardiac injection of pentobarbital sodium, following which their sciatic nerves were dissected free, harvested, and processed as previously described (Morrissey T K, et al., *J Neurosci* 1991;11: 2433–2442). Briefly, the nerves were placed into Liebovitz's L-15 medium (GIBCO) supplemented with 50 U/ml penicillin and 0.05 mg/ml streptomycin (L-15a). The epineurium, connective tissue, and blood vessels were stripped off with fine forceps. The nerves were placed in fresh L-15a and minced with scissors or scalpel blades into roughly 1×1 mm$^2$ explants. Minced nerves were placed in a 35-mm dish containing 1.25 U/ml dispase (Boehringer Mannheim Biochemicals), 0.05% collagenase (Worthington Biochemicals), 20% fetal bovine serum (FBS), and 25 mM HEPES in Dulbecco's Modified Eagle's Medium (DMEM,GIBCO). The tissue in this solution was triturated in a Pasteur pipette approximately 10 times and was then incubated overnight at 37° C. in a humidified atmosphere of air with 5% CO$_2$. The following day, the explants were dissociated by gentle trituration through a flame-narrowed borosilicate pipette (0.5–1-mm bore), washed 2–3 times in DMEM/10% FCS, and seeded into poly-D-lysine-coated (Sigma) tissue culture flasks (FALCON). To amplify the Schwann cell cultures, the cells were grown on poly-D-lysine-coated tissue culture plastic in DMEM supplemented with 10% FBS, 2 µM forskolin (Sigma) and 10 µg/ml bovine pituitary extract (GIBCO).

Schwann cells were identified in cultures on the basis of cell soma and nuclear morphology using phase microscopy. Cells with long bi- or tripolar processes (that were approximately 5–7 times the width of the cell body) and oval nuclei were counted as Schwann cells. In fixed cultures, we performed immunocytochemical labeling for S100 protein. Cells were fixed for 10 min in 4% paraformaldehyde followed by permeabilization in 4% paraformaldehyde with 0.02% Triton X-100. After blocking with L-15/10% heat-inactivated horse serum, the cells were incubated with a mouse monoclonal anti-S100 (b-subunit) antibody (1:1000; Sigma) overnight at 4° C. The following day, the cells were further processed by incubation with a biotinylated secondary horse anti-mouse antibody for 30 min at room temperature. Slides were then labeled with an Ultra Streptavidin Enzyme Complex (Signet Laboratories) according to the manufacturer's directions.

Schwann cell expression of VEGF and Flt-1 (VEGF receptor 1, or VEGFR-1) protein expression was assessed by Western blotting. Cells were lysed by addition of 1 ml RIPA buffer (1% NP-40, 0.5% sodium deoxycholic acid, 0.1% SDS in PBS, pH 7.4; 1 µM leupeptin; 5 µM aprotinin; 1 mM PMSA; and 1 µM pepstatin, all Sigma) per 100-mm plate. Protein extracts (100 µg) were separated on a 10% SDS-PAGE and transferred to a 0.2-µm PVDF membrane (Bio Rad). The membranes were blocked in 10% nonfat dry milk/0.2% Tween-20 in PBS, pH 7.4, then immunoblotted with a mouse monoclonal anti-human VEGF antibody (1:250) or a mouse monoclonal anti-human Flt-1 antibody (1:500) (both antibodies from Sigma) overnight at 4° C. Blots were washed with 0.2% Tween-20 in PBS and incubated with horseradish peroxidase-linked goat anti-mouse antibody (1:10000; Sigma) for 45 min. Imunoreactive bands were visualized with ECL reagent (Amersham). Very recent data from our laboratory has identified mRNA for both VEGFR2 (KDR) and neuropilin-1 in cultured Schwann cells as well.

We also assessed Schwann cell VEGF expression by ELISA testing upon the culture medium of equal numbers of cells in 24-well tissue culture plates. After the cells had grown to confluence, they were washed with DPBS and then further kept in DMEM containing various concentrations of cytokine- and growth factor-free defined FBS. After 24 hrs of incubation, equal volumes of supernatants from each test condition were removed, and the samples were cleared from cell debris by centrifugation (12000 rpm for 5 min). VEGF protein was determined with an immunoassay according to the manufacturer's instructions (R&D Systems). Results were compared with a standard curve of human VEGF with a lower detection limit of 5 µg/ml. Samples were checked by serial dilution and were performed in duplicate. The results are shown in Example Table 1.

EXAMPLE TABLE 1

ELISA measurement of VEGF protein (n = 2) for each condition

| | Defined FBS content in media | | | |
|---|---|---|---|---|
| | 0.5% | 1% | 5% | 10% |
| | $VEGF_{165}$ (pg/ml) | | | |
| Control medium | 12.6 | 9.2 | 1.1 | 63.4 |
| Cell culture supernatant | 851.5 | 759.8 | 1339.4 | 1935.5 |

Conclusion: Schwann cells express VEGF protein as well as VEGFR-1 (Flt-1) in vitro.

6. Schwann cell migration in response to VEGF

Methods and results: The migratory response of both primary and subcultured rabbit Schwann cells was assessed using a modified Boyden chamber assay (McCarthy J B, et al., *J Cell Biol* 1983;97:772–777) (Baron-Van Evercooren A, et al., *J Cell Biol* 1982;93:211–216). Schwann cells were detached from the tissue culture flasks with 0.05% trypsin/EDTA (GIBCO) and resuspended at $3 \times 10^5$/ml in chemotaxis medium (DMEM w/0.5% BSA, Sigma) before being placed in the upper well of a 48-well chemotaxis chamber (Neuroprobe). The lower wells of the chemotaxis chamber contained test reagents, which were reconstituted in chemotaxis medium. Upper and lower wells were separated by a 8-µm pore polyvinylpyrrolidone-free polycarbonate filter (Poretics), precoated with fibronectin (20 µg/ml). Chemotaxis chambers were incubated for 4 h at 37° C. in a humidified atmosphere of air with 5% $CO_2$. Thereafter, the filters were fixed and stained with Diff Qick (DADE). The filters were cut in half and mounted with the bottom side down (containing migrated cells) onto glass coverslips. Cells that had not migrated were removed from the upper surface with cotton swabs. After air drying, the coverslips were mounted onto glass slides and migration was quantified by counting migrated cells in 20 randomly selected high power (X400) fields. Each sample was assessed in quadruplicate, and results expressed as m±SEM chemotaxis index (CI, the ratio between the number of cells that migrated toward test substances and those which migrated toward medium control; migration toward medium reflects spontaneous migration). Zigmond-Hirsch checkerboard analysis (Zigmond S H, et al., *J Exp Med* 1973;137:387–410) was performed by incubating the cells in the chamber with various doses of test substances either on the bottom of the filter (to establish a positive gradient), on top of the filter (to establish a reversed gradient), or on both sides of the filter in equal concentrations (to examine accelerated random movement). Statistical significance of data was determined by Mann-Whitney U-test and Kruskal-Wallis-test for nonparametric analysis of results.

The chemotactic response of Schwann cells to graded concentrations of $rhVEGF_{165}$ protein was considered. VEGF stimulated migration in a dose-dependent manner, with maximal activity ranging from 10 to 1000 ng/ml. At these concentrations, approximately 1.8 times more cells migrated through the polycarbonate filter in comparison to the media control. At the lowest concentration tested (1 ng/ml), $rhVEGF_{165}$ still induced a statistically significant increase in chemotaxis with a CI of 1.3±0.04. Nerve growth factor (NGF, Sigma) served as positive chemoattractant control (Anton E S, et al., *Proc Natl Acad Sci USA* 1994;91: 2795–2799). To check for the specificity of this VEGF-induced effect, we performed additional experiments using a neutralizing monoclonal anti-VEGF antibody (Sigma). Results demonstrate that the antibody (dilution 1:500) itself had no effect on Schwann cell migration. When the antibody was present together with $rhVEGF_{165}$, we observed complete abrogation of the stimulatory effect of VEGF at 100 ng/ml as well as at 500 ng/ml were completely abrogated.

The migratory response of Schwann cells to VEGF could be explained either by chemotaxis (directed movement of cells along a chemotactic gradient) or by chemokinesis (enhanced speed or frequency of random migration). To address this issue, we performed a series of checkerboard analyses (Example Table 2). Addition of VEGF exclusively to the upper compartment together with Schwann cells failed to enhance migration; in contrast, gradually increasing the concentration gradient of VEGF between the lower and upper compartment increased migration of Schwann cells toward the lower compartment.

EXAMPLE TABLE 2

Checkerboard Analysis of rhVEGF$_{165}$-induced Schwann Cell Migration.

| | | VEGF (µg/ml), Upper compartment | | | |
|---|---|---|---|---|---|
| | | 0 | 1 | 100 | 500 |
| VEGF (µg/ml) Lower Compartment | 0 | 15.93 ± 1.1 | 15.05 ± 0.9 | 14.03 ± 0.9 | |
| | 1 | 16.40 ± 1.2 | 17.27 ± 0.8 | 17.02 ± 1.4 | 16.43 ± 1.1 |
| | 100 | 27.45 ± 0.8 | 24.87 ± 1.4 | 16.81 ± 1.1 | 17.93 ± 0.7 |
| | 500 | 33.90 ± 1.2 | 33.12 ± 2.2 | 27.56 ± 1.9 | 15.56 ± 1.6 |

Conclusion: VEGF directly promotes Schwann cell chemotaxis.

It should be understood that the preceding is merely a detailed description of certain preferred embodiments. It therefore should be apparent to those skilled in the art that various modifications and equivalents can be made without departing from the spirit and scope of the invention. The invention is intended to encompass all such modifications within the scope of the appended claims.

Example 5

Methods and results: Diabetes was induced in female Sprague Dawley rats by i.p. streptozotocin (85 mg/kg) according to previously published methods. Blood glucose was monitored repeatedly and animals were deemed diabetic if blood glucose exceeded 200 mg/dL. After a period of twelve weeks, the animals were treated with i.m. injections of either 250 micrograms of make plasmid DNA encoding for human VEGF$_{165}$, or saline. The effects of treatment were assessed after four weeks by recording sciatic nerve motor and sensory conduction velocities (M. Kalichman et al., Brain Res. 1998, 810:130–137). The motor nerve conduction velocity (MCV) of the untreated, non-diabetic group was 48.8±3.0 m/s (mean±SEM), and the sensory nerve conduction velocity (SCV) of this group was 62.0±4.9 m/s. The MCV of the saline-injected, diabetic group was 33.7±1.3 m/s and the SCV was 27.1±2.2 m/s. Therefore, MCV as well as SCV were significantly slowed in the diabetic (saline-injected) rats, as compared to the non-diabetic control animals. However, when rats were injected with ph VEGF$_{165}$, MCV was restored to 41.9±1.9 m/s, and SCV was improved to 59.5±7.0 m/s. Both MCV and SCV of the diabetic VEGF-treated group are significantly different from the corresponding parameters of the non-diabetic rats. Moreover, several non-diabetic rats were treated with ph VEGF$_{165}$ as a control, and neither MCV nor SCV were affected by this treatment.

Apfel et al. (Brain Res. 1994, 634:7–12) had reported that nerve growth factor (NGF) could ameliorate a sensory neuropathy caused by diabetes in streptozotocin-treated rats. These investigators administered recombinant human NGF three times weekly at a dose of 3 mg/kg. After 11 weeks, the compound latency as a measure of the conduction velocity of the caudal nerve in the tail was measured. The untreated diabetic rats had a mean compound latency of 1.85±0.09 m/s, while the NGF-treated diabetic rats had a mean compound latency of 1.76±0.04 m/s, and the control rats had a mean compound latency of 1.40±0.03. The rats from the treated group exhibited better nerve function compared to the untreated group but their NCVs were still significantly lower than those of the control group. We found that i.m. ph VEGF$_{165}$ was able to completely restore both motor and sensory NCVs within four weeks.

REFERENCES

Kalichman M W, Dines K C, Bobik M, Mizisin A P, Nerve conduction velocity, laser doppler flow, and axonal caliber in galactose and streptozotocin diabetes, Brain Res, 1998, 810:130–137.

Apfel S C, Arezzo J C, Brownlee M, Federoff H, Kessler J A, Nerve growth factor administration protects against experimental diabetic sensory neuropathy.

All references, patents and patent publications that are recited in this application are incorporated in their entirety herein by reference.

---

---

The invention claimed is:

1. A method for treating an ischemic peripheral neuropathy in a subject, comprising:

administering at least one nucleic acid encoding a vascular endothelial growth factor (VEGF) to a subject having ischemic peripheral neuropathy in an amount effective to alleviate a symptom of peripheral neuropathy in the subject, wherein the subject is free of symptoms calling for treatment with an angiogenic growth factor except for having the ischemic peripheral neuropathy, and wherein the administering is by intramuscular administration.

2. The method of claim 1, wherein the administering further comprises administering a nucleic acid encoding a basic fibroblast growth factor (bFGF) to the subject.

3. The method of claim 1, wherein the VEGF is selected from the group consisting of:

(a) VEGF A;
(b) VEGF B;
(c) VEGF C;
(d) VEGF D;
(e) $VEGF_{121}$;
(f) $VEGF_{145}$;
(g) $VEGF_{165}$; and
(h) $VEGF_{189}$.

4. The method of claim 1, wherein the ischemic peripheral neuropathy is a diabetic peripheral neuropathy.

* * * * *

UNITED STATES PATENT AND TRADEMARK OFFICE
CERTIFICATE OF CORRECTION

PATENT NO. : 7,125,856 B1 Page 1 of 1
APPLICATION NO. : 09/546733
DATED : October 24, 2006
INVENTOR(S) : Jeffrey M. Isner It is certified that error appears in the above-identified patent and that said Letters Patent is hereby corrected as shown below:

On the title page item (73), Assignee should be changed from "St. Elizabeth's Medical Center of Boston, Inc., Boston, MA (US)" to --Caritas St. Elizabeth's Medical Center of Boston, Inc., Boston, MA (US)--

Signed and Sealed this

Ninth Day of January, 2007

JON W. DUDAS
*Director of the United States Patent and Trademark Office*